(12) United States Patent
Zukowski et al.

(10) Patent No.: US 8,469,621 B2
(45) Date of Patent: Jun. 25, 2013

(54) PERSONAL CARE PRODUCT HAVING A SOLID PERSONAL CARE COMPOSITION WITHIN A STRUCTURE MAINTAINING DISPENSER

(75) Inventors: Joseph Michael Zukowski, Cincinnati, OH (US); Nancy Lorincz Leppla, Loveland, OH (US); Chu Zhu, Cincinnati, OH (US); Ann Marie Cilley, Mason, OH (US); Laurie Ellen Breyfogle, Milford, OH (US)

(73) Assignee: The Procter & Gamble Company, Cincinnati, OH (US)

(*) Notice: Subject to any disclaimer, the term of this patent is extended or adjusted under 35 U.S.C. 154(b) by 1230 days.

(21) Appl. No.: 12/037,536

(22) Filed: Feb. 26, 2008

(65) Prior Publication Data

US 2009/0003920 A1    Jan. 1, 2009

Related U.S. Application Data

(60) Provisional application No. 60/903,634, filed on Feb. 27, 2007.

(51) Int. Cl.
*B43K 1/06* (2006.01)

(52) U.S. Cl.
USPC .............................. 401/265; 401/261; 401/171

(58) Field of Classification Search
USPC .................. 401/171, 150, 261, 263, 265, 266
See application file for complete search history.

(56) References Cited

U.S. PATENT DOCUMENTS

| | | | |
|---|---|---|---|
| 2,656,953 A * | 10/1953 | Rich | ............................. 222/390 |
| 3,563,414 A | 2/1971 | Coulombe | |
| 4,120,948 A | 10/1978 | Shelton | |
| 4,159,028 A | 6/1979 | Barker | |
| 4,335,103 A | 6/1982 | Barker | |
| 4,578,266 A | 3/1986 | Tietjen | |
| 4,781,917 A | 11/1988 | Luebbe | |

(Continued)

FOREIGN PATENT DOCUMENTS

| | | |
|---|---|---|
| DE | 633401 | 7/1936 |
| EP | 374332 B1 | 1/1993 |

(Continued)

OTHER PUBLICATIONS

Microfilm of the Specifications and Drawings Annexed to the Request of Japanese Utility, Model Application No. 46123-1990 (Laid-open No. 7476/1992); Pola Chemical Industries, Inc. Jan. 23, 1992; Full text; all drawings.

(Continued)

*Primary Examiner* — David Walczak
(74) *Attorney, Agent, or Firm* — S. Robert Chuey

(57) ABSTRACT

A personal care product having a personal care composition and a dispensing container with the personal care composition disposed therein. The personal care composition may have a pre-dispense G' of at least about 5,000 Pa. The personal care product provides a G' preservation percentage of no less than 10%. The dispensing container can be a container body having a storage void containing the personal care composition, a movable partition at least partially disposed within the storage void, a drive mechanism connected to and able to advance the movable partition, and a dispensing plate joined to the container body. The dispensing plate has an orifice through which the personal care composition is dispensed. The orifice may have an inscribed circle diameter of about 1 mm to about 12 mm.

17 Claims, 9 Drawing Sheets

U.S. PATENT DOCUMENTS

| | | | |
|---|---|---|---|
| 4,782,983 A | 11/1988 | Cook | |
| 4,966,205 A | 10/1990 | Tanaka | |
| 4,970,252 A | 11/1990 | Sakuta | |
| 4,980,155 A | 12/1990 | Shah | |
| 5,000,356 A | 3/1991 | Johnson | |
| 5,007,755 A | 4/1991 | Thompson | |
| 5,019,375 A | 5/1991 | Tanner | |
| 5,059,414 A | 10/1991 | Dallal | |
| 5,066,485 A | 11/1991 | Brieva | |
| 5,304,334 A | 4/1994 | Lahanas | |
| 5,362,482 A | 11/1994 | Yoneyama | |
| 5,413,781 A | 5/1995 | Giwa Agbomeirele | |
| 5,547,302 A | 8/1996 | Dornbusch | |
| 5,654,362 A | 8/1997 | Schulz | |
| 5,720,416 A * | 2/1998 | Izoe | 222/138 |
| 5,725,845 A | 3/1998 | Krog | |
| 5,750,096 A | 5/1998 | Guskey | |
| 5,760,116 A | 6/1998 | Kilgour | |
| 5,882,657 A | 3/1999 | Miguel | |
| 5,961,007 A | 10/1999 | Dornbusch | |
| 6,039,935 A | 3/2000 | Mohammadi | |
| 6,143,284 A | 11/2000 | Bush | |
| 6,159,485 A | 12/2000 | Yu | |
| 6,207,596 B1 | 3/2001 | Rourke | |
| 6,213,166 B1 | 4/2001 | Thibiant | |
| 6,245,344 B1 | 6/2001 | Thibiant | |
| 6,268,322 B1 | 7/2001 | St. Lewis | |
| 6,331,306 B1 | 12/2001 | Afriat | |
| 6,367,519 B2 | 4/2002 | Thibiant | |
| 6,488,941 B1 | 12/2002 | Burnier | |
| 6,492,326 B1 | 12/2002 | Robinson | |
| 6,503,944 B1 | 1/2003 | Chanchani | |
| 6,516,838 B2 | 2/2003 | Thibiant | |
| 6,524,598 B2 | 2/2003 | Sunkel | |
| 6,696,049 B2 | 2/2004 | Vatter | |
| 6,905,695 B1 | 6/2005 | Afriat | |
| 7,005,557 B2 | 2/2006 | Klofta | |
| 7,329,403 B2 | 2/2008 | Chuah | |
| 7,449,613 B2 | 11/2008 | Klofta | |
| D608,655 S | 1/2010 | Brewer | |
| 7,681,320 B2 | 3/2010 | Szczepanowski | |
| D613,614 S | 4/2010 | Rodriguez | |
| D615,868 S | 5/2010 | Rodriguez | |
| D621,515 S | 8/2010 | Chua | |
| D634,435 S | 3/2011 | Chua | |
| D640,925 S | 7/2011 | Rodriguez | |
| D641,250 S | 7/2011 | Daniels | |
| 2002/0028184 A1 | 3/2002 | Sunkel | |
| 2002/0037302 A1 | 3/2002 | Afriat | |
| 2002/0127192 A1 | 9/2002 | Murphy | |
| 2002/0182237 A1 | 12/2002 | Bissett | |
| 2003/0049212 A1 | 3/2003 | Robinson | |
| 2003/0082219 A1 | 5/2003 | Warren | |
| 2003/0111130 A1 | 6/2003 | Dugdale | |
| 2003/0143169 A1 | 7/2003 | Elliott | |
| 2003/0206943 A1 | 11/2003 | Hammons | |
| 2004/0057920 A1 | 3/2004 | Focht | |
| 2004/0170589 A1 | 9/2004 | Gatto | |
| 2004/0175347 A1 | 9/2004 | Bissett | |
| 2004/0192649 A1 | 9/2004 | Bissett | |
| 2004/0228820 A1 | 11/2004 | Elliott | |
| 2005/0003024 A1 | 1/2005 | Oblong | |
| 2005/0129651 A1 | 6/2005 | Gatto | |
| 2005/0148962 A1 | 7/2005 | Warren | |
| 2005/0154362 A1 | 7/2005 | Warren | |
| 2005/0255059 A1 | 11/2005 | Oblong | |
| 2006/0062816 A1 | 3/2006 | Gatto | |
| 2006/0127431 A1 | 6/2006 | Oblong | |
| 2006/0188462 A1 | 8/2006 | Bissett | |
| 2006/0188467 A1 | 8/2006 | Bissett | |
| 2006/0193809 A1 | 8/2006 | Bissett | |
| 2006/0246317 A1 | 11/2006 | Lyu | |
| 2006/0275237 A1 | 12/2006 | Bissett | |
| 2007/0053858 A1 | 3/2007 | Tanner | |
| 2007/0128137 A1 | 6/2007 | Yoshimi | |
| 2007/0264210 A1 | 11/2007 | Robinson | |
| 2007/0274932 A1 | 11/2007 | Suginaka | |
| 2007/0286876 A1 | 12/2007 | Warren | |
| 2007/0297996 A1 | 12/2007 | Tanner | |
| 2007/0297997 A1 | 12/2007 | Tanner | |
| 2008/0025932 A1 | 1/2008 | Bissett | |
| 2008/0038216 A1 | 2/2008 | Zukowski | |
| 2008/0038360 A1 | 2/2008 | Zukowski | |
| 2008/0188505 A1 | 8/2008 | Oblong | |
| 2009/0003920 A1 | 1/2009 | Zukowski | |
| 2009/0011035 A1 | 1/2009 | Zukowski | |
| 2009/0041697 A1 | 2/2009 | Klofta | |
| 2010/0092405 A1 | 4/2010 | Philippe | |
| 2010/0092408 A1 | 4/2010 | Breyfogle | |
| 2010/0119619 A1 | 5/2010 | Griffiths-Brophy | |
| 2010/0297996 A1 | 11/2010 | Yokota | |
| 2010/0303744 A1 | 12/2010 | Breyfogle | |
| 2010/0305168 A1 | 12/2010 | Robinson | |
| 2010/0305169 A1 | 12/2010 | Robinson | |
| 2011/0020250 A1 | 1/2011 | Breyfogle | |

FOREIGN PATENT DOCUMENTS

| | | | |
|---|---|---|---|
| EP | 1166746 B1 | 7/2003 | |
| EP | 1068852 B1 | 9/2004 | |
| JP | 6118708 | 4/1994 | |
| JP | 2003055141 | 2/2003 | |
| JP | 2005023360 | 1/2005 | |
| WO | WO02100358 | 12/2002 | |
| WO | WO02076423 | 3/2003 | |
| WO | WO2004078157 | 9/2004 | |
| WO | WO2006075484 | 7/2006 | |

OTHER PUBLICATIONS

Microfilm of the Specifications and Drawings Annexed to the Request of Japanese Utility, Model Application No. 66057/1972 (Laid Open No. 26384/1974) Daiichi Pharmaceutical Co., Ltd., Mar. 6, 1974; Full text, all drawings.

Microfilm of the Specifications and Drawings Annexed to the Request of Japanese Utility, Model Application No. 106784/1982 (Laid-open No. 10714/1984) Yoshino Kogyosho Co. Ltd.; Jan. 23, 1984; p. 4, line 17 to p. 5, line 1; Fig. 2.

International Search Report, PCT/IB2008/050707, mail date Nov. 11, 2010; 5 pages.

* cited by examiner

PERSONAL CARE PRODUCT HAVING A SOLID PERSONAL CARE COMPOSITION WITHIN A STRUCTURE MAINTAINING DISPENSER

CROSS REFERENCE TO RELATED APPLICATION

This application claims the benefit of provisional application No. 60/903,634, filed Feb. 27, 2007.

FIELD OF THE INVENTION

The present invention relates to solid personal care compositions and dispensers that maintain the solid character of the personal care compositions during dispensing.

BACKGROUND OF THE INVENTION

A variety of personal care compositions are available to the consumer to provide skin care benefits and to counteract what many consider undesirable "signs of skin aging," such as fine lines, wrinkles and uneven skin texture. Personal care compositions may provide chronic benefits that materialize over a prescribed period of time. To be most effective, these products must be applied regularly and over an extended period of time. To encourage routine usage, it is important that the product have a desirable appearance and a pleasant feel when applied. Consumers desiring more benefit and/or protection often will choose a thicker product. For example, a cream composition tends to be perceived as offering greater anti-aging benefits than a lotion. However, creams tend to have a heavy feel, and may be undesirable for use during the day, under make-up, or during warm and/or humid weather conditions. Other product forms such as milks or oils tend to run rapidly off the skin surface and may soil surrounding clothing or other surfaces before the product can be sufficiently rubbed into the skin. It is desirable to provide creamy personal care composition having solid physical characteristics that maybe applied and rubbed into the skin.

Existing solid personal care compositions often incorporate solidifying agents but such solidifying agents provide formulation trade-offs. For example, solidifying agents having the best thermal stability often do not result in personal care compositions having good rub-in characteristics. Alternatively, certain solidifying agents, which have reduced thermal stability, often yield personal care compositions having good rub-in and skin absorbency. The skin care products having these later types of solidifying agents may be formulated with improved thermal stability through rheological modification such as internal phase packing when a large volume of a dispersed or emulsified internal phase thickens or through the inclusion of an elastomer.

Storage and delivery presents another issue for skin care compositions having a solid character. Even if a solid personal care composition is formulated to exhibit thermal stability and to have good rub-in characteristics, the solid personal care composition may be adversely affected by the delivery device (e.g., solid character is destroyed, phases separate, etc.). Traditional open mouth jars may be a suitable container, but are generally disfavored by consumers. Open mouth jars are viewed as less sanitary since jars lack a dispensing means. Instead, a user must dip a finger or other implement into the composition in order to remove a portion for application and may become soiled, adulterated, or contaminated. Furthermore, open jars provide no mechanism for metering a portion of the composition for application; this results in fluctuations in the amount of composition used from one application to the next. Pumps containers solve many of the problems associated with open mouth jars by providing a sanitary means for dispensing a prescribed amount of a composition. However, many conventional pumps present problems delivering compositions having requisite thermal stability while also containing solidifying agents with advantageous rub-in characteristics. Many pumps are simply unable to reliably dispense skin care compositions that have a solid character. The pump mechanism has difficulty in transporting thick, viscous skin care compositions. Even if the pump is able to dispense the skin care composition, the pump often adversely affects the solid character of the composition upon dispensation. It is believed that the pump mechanism and process disturb the balance achieved between solid character, thermal stability, and good rub-in characteristics. The net result being that the composition shears and loses a significant portion of the solid character during pumping.

Therefore, a need exists to provide a personal care product comprising a personal care composition, which has a solid character that conveys increased benefit and provide improved skin feel, in a dispensing container that retains the unique characteristics of the composition.

SUMMARY OF THE INVENTION

In light of the needs presented above, the present invention relates to a personal care product comprising a personal care composition and a dispensing container having the personal care composition disposed therein. The personal care composition may have a pre-dispense G' of at least about 5,000 Pa. The dispensing container may comprise a container body having a storage void containing the personal care composition, a movable partition at least partially disposed within the storage void, a drive mechanism connected to and able to advance the movable partition, and a dispensing plate joined to the container body. The dispensing plate has an orifice through which the personal care composition is dispensed. The personal care product provides a G' preservation percentage of no less than 10%.

The present invention further relates to a personal care product comprising a personal care composition and a dispensing container having the personal care composition disposed therein. The personal care composition has a pre-dispense G' of at least about 5,000 Pa. The dispensing container comprises a container body having a storage void containing the personal care composition and an orifice through which the personal care composition is dispensed from the storage void. The orifice has an inscribed circle diameter of about 1 mm to about 12 mm. The personal care product provides a G' preservation percentage of no less than 10%.

The present invention further relates to a personal care product comprising a personal care composition and a dispensing container having the personal care composition disposed therein. The personal care composition has a pre-dispense G' of at least about 5,000 Pa and comprises from about 0.1% to about 15% of an emulsifying silicone elastomer; from about 0.1% to about 40% of at least one solidifying agent; from about 1% to about 75% of an aqueous phase; and at least one skin care active selected from the group consisting of vitamin B compounds, vitamin C compounds, vitamin E compounds, peptides, sugar amines, oil control agents, skin lightening agents, hexamidine, and combinations thereof. The dispensing container has the personal care composition disposed therein. The personal care product provides a G' preservation percentage of no less than 10%.

The present invention further relates other embodiments of the personal care product as provided in the Detailed Description.

BRIEF DESCRIPTION OF THE DRAWINGS

In the accompanying drawings, like reference numerals may identify like elements. However, elements may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

DETAILED DESCRIPTION OF THE INVENTION

Figure 1A:
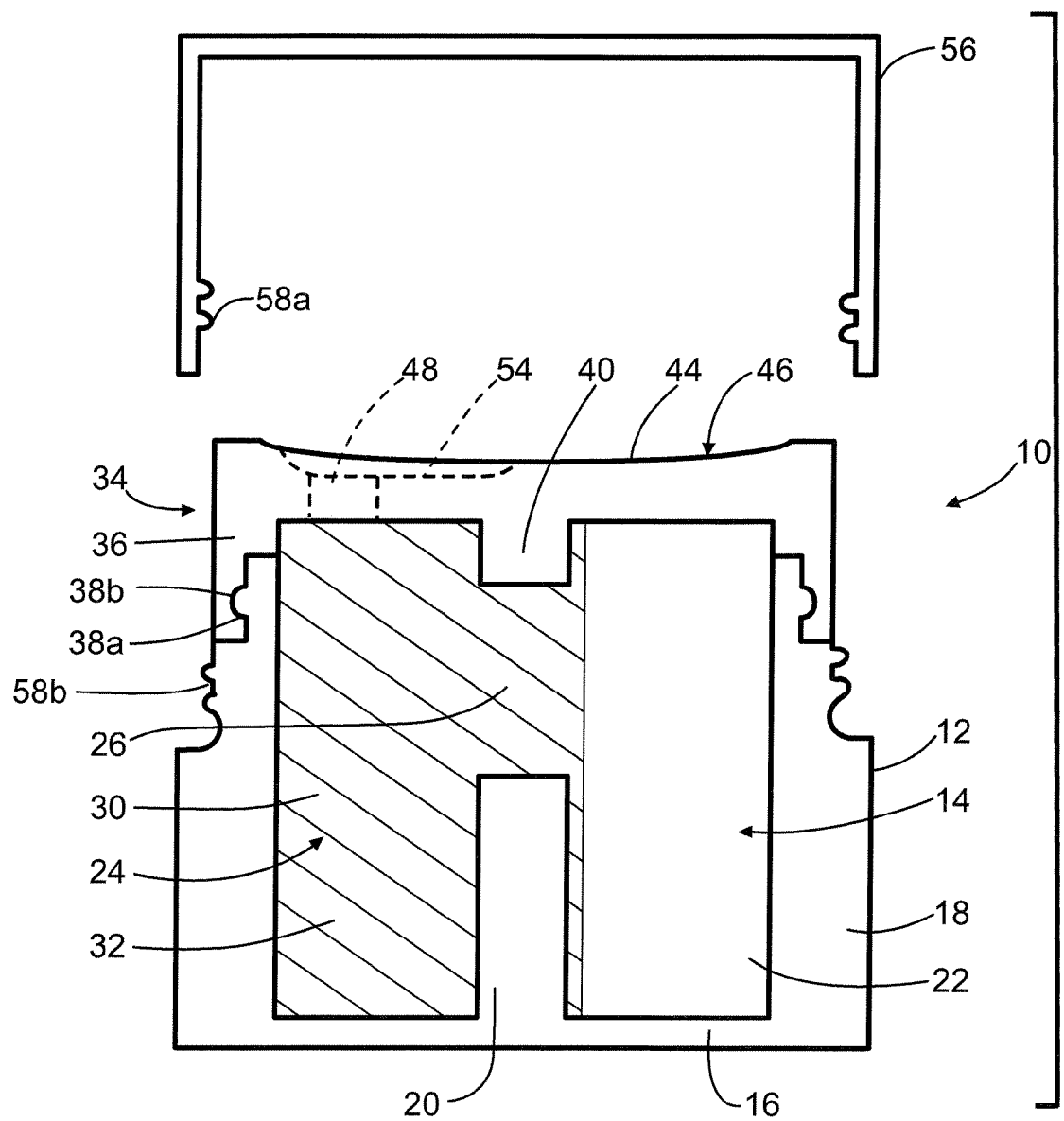
FIG. 1A is a cross-sectional view of an embodiment of a dispensing container.

As used herein, the following terms shall have the meaning specified thereafter. It should be recognized that capitalization of the listed terms is predicated on grammar and capitalization of the terms may not be continued throughout the remaining of the text.

"Personal care composition" means compositions suitable for topical application on mammalian keratinous tissue.

"Skin care actives," or "actives," as used herein, means compounds that, when applied to the skin, provide a benefit or improvement to the skin. It is to be understood that skin care actives are useful not only for application to skin, but also to hair, nails, and other mammalian keratinous tissue.

"Dispensing container" refers a device that contains a personal care composition and dispenses a portion of the personal care composition.

"Safe and effective amount" means an amount of a compound or composition sufficient to induce a positive benefit but low enough to avoid serious side effects (i.e., provides a reasonable benefit to risk ratio within the judgment of a skilled artisan).

"Stable" and "stability" mean a composition which is substantially unaltered in chemical state, physical homogeneity, and/or color when the composition is at a temperature of from about 1° C. to about 40° C.

"Keratinous tissue" refers to keratin-containing layers disposed as the outermost protective covering of mammals including, but is not limited to, skin, hair, nails, cuticles, etc.

"Applied" or "application" means to spread the composition onto keratinous tissue with one or more fingers and/or an implement as one would be expected to apply a cream to the facial skin.

"Regulating skin condition" means improving skin appearance and/or feel, for example, by providing a benefit, such as a smoother appearance and/or feel. Herein, "improving skin condition" means effecting a visually and/or tactilely perceptible positive change in skin appearance and feel. The benefit may be a chronic or acute benefit and may include one or more of the following: Reducing the appearance of wrinkles and coarse deep lines, fine lines, crevices, bumps, and large pores; thickening of keratinous tissue (e.g., building the epidermis and/or dermis and/or sub-dermal layers of the skin, and where applicable the keratinous layers of the nail and hair shaft, to reduce skin, hair, or nail atrophy); increasing the convolution of the dermal-epidermal border (also known as the rete ridges); preventing loss of skin or hair elasticity, for example, due to loss, damage and/or inactivation of functional skin elastin, resulting in such conditions as elastosis, sagging, loss of skin or hair recoil from deformation; reduction in cellulite; change in coloration to the skin, hair, or nails, for example, under-eye circles, blotchiness (e.g., uneven red coloration due to, for example, rosacea), sallowness, discoloration caused by hyperpigmentation, etc.

"Signs of skin aging," include, but are not limited to, all outward visibly and tactilely perceptible manifestations, as well as any macro- or micro-effects, due to keratinous tissue aging. These signs may result from processes which include, but are not limited to, the development of textural discontinuities such as wrinkles and coarse deep wrinkles, fine lines, skin lines, crevices, bumps, large pores, unevenness or roughness; loss of skin elasticity; discoloration (including undereye circles); blotchiness; sallowness; hyperpigmented skin regions such as age spots and freckles; keratoses; abnormal differentiation; hyperkeratinization; elastosis; collagen breakdown, and other histological changes in the stratum corneum, dermis, epidermis, vascular system (e.g., telangiectasia or spider vessels), and underlying tissues (e.g., fat and/or muscle), especially those proximate to the skin.

"Insult-affected keratinous tissue," means keratinous tissue which exhibits discomfort, irritation, an unpleasant or irregular appearance, and the like, for example after exposure to a physical and/or chemical irritant. Non-limiting examples of insult-affected keratinous tissue include sunburn and other types of burns; rashes, such as diaper rash, shaving rash and allergen-induced rashes; discoloration, such as bleaching, staining or hyperpigmentation; skin having nicks and cuts due to, for example, shaving; dry, chapped or rough skin due to exposure to example wind, cold and/or low humidity, etc. Non-limiting examples of insults include radiation, wind, low humidity, allergens, pollutants, chemical and natural irritants, bodily fluids, bodily waste, excessive moisture, bacteria, fungi, etc.

"Non-volatile" means materials that exhibit a vapor pressure of no more than about 0.2 mm Hg at 25° C. at one atmosphere and/or to materials that have a boiling point at one atmosphere of at least about 300° C. "Volatile," as used herein, all materials that are not "non-volatile" as defined herein.

"Non-polar" means that the material has an average solubility parameter below about 6.5 $(cal/cm^3)^{0.5}$, where "cal" means calories. Oils having a higher solubility parameter than 6.5 may be used if, when the oils are blended with other oils, the weighted average of the solubility parameter of the oil blend is below about 6.5. Herein, "weighted average" means that the volumes and the solubility parameters of the various oils are taken into account when calculating the average solubility parameter. "Polar," as used herein means that the material has a higher average solubility parameter than non-polar compounds as defined herein.

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. All measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

I. Personal Care Composition

The personal care composition of the present invention may be used in skin care, cosmetic, and hair care products, non-limiting uses of which include moisturizers, conditioners, anti-aging compounds, skin lightening compounds, and combinations thereof. In certain embodiments, the composition is applied to the face, neck, hands, arms, and other typically exposed areas of the body. Alternatively, the composition is applied to insult-affected areas of keratinous tissue.

The compositions of the present invention are useful for improving skin appearance and/or feel. The compositions of the present invention may be useful for regulating skin condition and/or improving skin condition. In certain particular embodiments, the composition is useful for regulating and/or improving the signs of skin aging. The compositions may provide an essentially immediate (i.e., acute) improvement in skin appearance and/or feel following application. It is believed that the acute improvement may be attained with a single or limited number of applications of the composition. However, the compositions may comprise components that provide a gradual (i.e., chronic) improvement in skin appearance and/or feel. It is believed that the chronic improvement may involve multiple, reoccurring, or periodic applications of the composition. The compositions of the present invention may also be incorporated into consumer products that facilitate the application of the composition. In certain embodiments, the consumer products allow the composition to be applied as a spot treatment over a limited area of the skin.

The personal care composition may be provided in a wide variety of forms. Non-limiting examples include simple solutions (water or oil based), emulsions, and gels. In certain embodiments, the personal care composition is in the form of an emulsion comprising a non-aqueous phase and an aqueous phase. The composition may comprise from about 25% to about 99% or from about 30% to about 70%, of the non-aqueous phase. Suitable types of emulsions include, but are not limited to, oil-in-water, water-in-oil, water-in-oil-in-water, and oil-in-water-in-oil emulsions. Suitable oils include silicone oils, non-silicone oils such as hydrocarbon oils, esters, ethers, and the like, and mixtures thereof. In one embodiment, the composition is in the form of a water-in-oil emulsion. In one embodiment, the composition is a water-in-silicone emulsion.

In one embodiment, the composition comprises from about 1% to about 75% or from about 30% to about 70%, of an aqueous phase. In certain embodiments, the aqueous phase may comprise about 0.1% to about 100% water. In other embodiments, the aqueous phase may comprise from about 0.1% to about 100% of a non-water diluent including but not limited to water-soluble moisturizing agents, conditioning agents, humectants and/or other water-soluble skin care actives, to impart an increased benefit to the keratinous tissue. In one embodiment, the non-water diluent consists of glycerin, water-soluble skin care actives, and combinations thereof. In one embodiment, the non-water component is glycerin and/or other polyols.

The composition of the present invention may exhibit a pre-dispense G'. As is well recognized, G' is the storage modulus (or elastic modulus) of a material. The term "pre-dispense G'" refers the G' of a personal care composition within a container as measured according to the test method provided below. In measuring the pre-dispense G', it may be necessary to open the container, which, in some cases may adversely affect the ability of the container to dispense the personal care composition. In such cases, the pre-dispense G' and post-dispense G' (as defined below) may be performed on separate but substantially similar consumer products (i.e., replicates).

The personal care composition may exhibit a pre-dispense G' of at least about 5,000 Pa. In other embodiments, the personal care composition may exhibit a pre-dispense G' of at least about 10,000 Pa, about 25,000 Pa, or, alternatively, about 50,000 Pa. A personal care composition is considered "solid" if the personal care composition exhibits a pre-dispense G' of at least one of the aforementioned values. In certain embodiments, it may be desirable that the pre-dispense G' not exceed 350,000 Pa, 300,000 Pa, 275,000 Pa, or, alternatively, 200,000 Pa.

The composition of the present invention may be stable.

A. Elastomers

The composition of the present invention comprises a silicone elastomer, useful for reducing the tackiness of the composition and for providing a pleasant feel upon application. One non-limiting example of useful silicone elastomers is crosslinked organopolysiloxane (or siloxane) elastomers, as described in U.S. patent publication 2003/0049212A1. The elastomers may comprise emulsifying and non-emulsifying silicone elastomers. "Emulsifying," as used herein, means crosslinked organopolysiloxane elastomers having at least one polyoxyalkylene (e.g., polyoxyethylene or polyoxypropylene) or polyglycerin moiety, whereas "non-emulsifying" means crosslinked organopolysiloxane elastomers essentially free of polyoxyalkylene or polyglycerin moieties.

The composition of the present invention may comprise from about 0.1% to about 15%, alternatively from about 0.1% to about 5%, and alternatively from about 0.1% to about 2% of a non-emulsifying crosslinked siloxane elastomer. The indicated percentages are understood to refer to amount of dry elastomer, as opposed to the total amount of elastomer and solvent, used for example for storage and shipping. In one embodiment, the non-emulsifying crosslinked siloxane elastomers are dimethicone/vinyl dimethicone crosspolymers, supplied by a variety of suppliers including Dow Corning™ (DC 9040, DC 9041, and DC 9045), General Electric™ (SFE 839), Shin Etsu™ (KSG-15, 16, 18 [dimethicone/phenyl vinyl dimethicone crosspolymer]), and Grant Industries (GRANSIL™ line of elastomers). Cross-linked siloxane elastomers useful in the present invention and processes for making them are further described in U.S. Pat. No. 4,970,252 to Sakuta, et al.; U.S. Pat. No. 5,760,116 to Kilgour, et al.; and U.S. Pat. No. 5,654,362 to Schulz, Jr., et al. issued Aug. 5, 1997. Additional crosslinked organopolysiloxane elastomers useful in the present invention are disclosed in Japanese Patent Application JP 61-18708, assigned to Pola Kasei Kogyo KK.

The composition of the present invention may comprise from about 0.1% to about 15%, alternatively from about 0.2% to about 5%, and alternatively from about 0.2% to about 2% of an emulsifying crosslinked organopolysiloxane elastomer, described in U.S. Pat. Nos. 5,412,004; 5,837,793; and 5,811,487. Suitable emulsifying crosslinked organopolysiloxane elastomers include dimethicone/PEG-10 crosspolymers such as KSG 24; dimethicone/PEG-10 crosspolymers such as KSG 21 and KSG 210; PEG-15/lauryl dimethicone crosspolymers such as KSG 31, KG 32, KSG 33, KSG 310, KG 320, KSG 330; PEG-15/lauryl dimethicone crosspolymers and PEG-10/lauryl dimethicone crosspolymers such as KSG 34 and KSG 340; dimethicone/polyglycerine-3 crosspolymers such as KSG-710; and lauryl dimethicone/polyglycerine-3 crosspolymers such as KSG 810, KSG 820, KSG 830, and KSG 840. All KSG materials are available from Shin Etsu™.

B. Elastomer Solvent

The composition of the present invention may comprise from about 1% to about 70%, from about 4% to about 55%, from about 5% to about 45%, or alternatively from about 10% to about 40%, of a suitable solvent for the crosslinked organopolysiloxane elastomers. Non-limiting examples of suitable solvents are described in U.S. patent publication 2003/0049212A1. The concentration of the solvent in the cosmetic compositions of the present invention may vary depending upon the type and amount of solvent and the cross-linked siloxane elastomer employed, and when combined with the cross-linked organopolysiloxane elastomer particles of the present invention, suspends and swells the elastomer particles to provide an elastic, gel-like network or matrix. The carrier for the cross-linked siloxane elastomer is liquid under ambient conditions, and in one embodiment has a low viscosity to provide for improved spreading on the skin.

The solvent may comprise volatile, non-polar oils; non-volatile, polar oils; non-volatile, non-polar oils; and non-volatile paraffinic hydrocarbon oils. Non-limiting examples of suitable non-polar, volatile oil are disclosed in U.S. Pat. No. 4,781,917 issued to Luebbe et al. and include polydecanes such as isododecane and isodecane (e.g., Permethyl-99A, available from Presperse™ Inc.) and C7-C15 isoparaffins (e.g., the Isopar Series, from Exxon™ Chemicals); cyclomethicones of varying viscosities, e.g., Dow Corning™ 200, Dow Corning™ 244, Dow Corning™ 245, Dow Corning™ 344, and Dow Corning™ 345, Silicone Fluids, commercially available from G.E. Silicones, (e.g., SF-1204, SF-1202, GE 7207 and GE 7158); and SWS-03314 (commercially available from SWS Silicones™ Corp.).

Polar, non-volatile oils useful in the present invention include, but are not limited to, silicone oils; hydrocarbon oils; fatty alcohols; fatty acids; esters of mono and dibasic carboxylic acids with mono and polyhydric alcohols; polyoxyethylenes, polyoxypropylenes, mixtures of polyoxyethylene and polyoxypropylene ethers of fatty alcohols; and mixtures thereof. In one embodiment, the polar, non-volatile oil is selected from the group consisting of propoxylated ethers of C14-C18 fatty alcohols having a degree of propoxylation below about 50, esters of C2-C8 alcohols and C12-C26 carboxylic acids (e.g., ethyl myristate, isopropyl palmitate), esters of C12-C26 alcohols and benzoic acid (e.g., Finsolv™ TN supplied by Finetex™), diesters of C2-C8 alcohols and adipic, sebacic, and phthalic acids (e.g., diisopropyl sebacate, diisopropyl adipate, di-n-butyl phthalate), polyhydric alcohol esters of C6-C26 carboxylic acids (e.g., propylene glycol dicaprate/dicaprylate, propylene glycol isostearate); and mixtures thereof.

Examples of suitable non-volatile, non-polar oils include, but are not limited to non-volatile polysiloxanes, paraffinic hydrocarbon oils, and mixtures thereof. The polysiloxanes useful in the present invention selected from the group consisting of polyalkylsiloxanes, polyarylsiloxanes, polyalkylarylsiloxanes, poly-ethersiloxane copolymers, and mixtures thereof. Examples of useful oils include Viscasil™ series (General Electric); the Dow Corning 200 series (Dow Corning Corp.); SF 1075 methyl-phenyl fluid (General Electric) and 556 Cosmetic Grade Fluid (Dow Corning Corp.).

Non-volatile paraffinic hydrocarbon oils useful in the present invention are described in U.S. Pat. No. 5,019,375 issued to Tanner et al. and in 2003/0049212A1, and include mineral oils and branched-chain hydrocarbons such as Permethyl™ 102A, 103A and 104A (Permethyl Corporation); and Ethylflo™ 364 (Ethyl Corp.). Additional suitable solvents useful herein are described in U.S. Pat. No. 5,750,096 to Guskey et al.

C. Emulsifier

The composition of the present invention may contain an additional emulsifier, useful for dispersing and suspending the aqueous phase within the oil phase in a water-in-oil emulsion. The composition may comprise from about 0.001% to about 5%, alternatively from about 0.01% to about 5% alternatively from about 0.1% to about 3%, alternatively from about 0.1% to about 2%, and alternatively from about 0.1% to about 1%, of at least one additional emulsifier.

A wide variety of emulsifying agents can be employed herein to form a water-in-silicone emulsion, and are described in U.S. patent publication 2003/0049212A1. In one embodiment, the additional emulsifiers are silicone emulsifiers, including organically modified organopolysiloxanes (silicone surfactants) such as dimethicone copolyols. Examples of commercially available dimethicone copolyols useful herein are Dow Corning®190, 193, Q2-5220, 2501 Wax, 2-5324 fluid, and 3225C; ABIL™ EM-90, ABIL™ WE-09 and ABIL™ WS-08 (Goldschmidt), KF-6028 and KF-6106 (Shin-Etsu™).

In one embodiment, the additional emulsifier is a non-silicone emulsifier, non-limiting examples of which include non-ionic and anionic emulsifying agents such as sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, soaps, and mixtures thereof.

D. Solidifying Agent

The composition of the present invention comprises one or more solidifying agents suitable to impart stability to the composition and to impart a suitable solid character as determined by G'. A variety of suitable solidifying agents may be used, including those disclosed in U.S. Pat. No. 6,696,049, issued to Vatter et al. In one embodiment, the solidifying agent is a wax. The composition may comprise from about 0.1% to about 40%, from about 0.5% to about 20%, from about 1% to about 5%, or, alternatively, from about 5% to about 15%, of one or more solidifying agents.

Waxes suitable for use herein include but are not limited to animal, vegetable, mineral, or silicone waxes. Generally such waxes have a melting point ranging from about 25° C. to 125° C., and alternatively from about 30° C. to about 100° C.

Non-limiting examples of suitable waxes include silicone waxes, synthetic waxes such as hydrocarbon polymers and hydrocarbon waxes fatty esters, for example cetyl and/or stearyl esters, acacia, beeswax, ceresin, flower wax, citrus wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, candelilla, grape wax, polyalkylene glycol derivatives thereof (for example PEG6-20 beeswax, or PEG-12 carnauba wax) and mixtures of any of the aforementioned waxes. In one embodiment, the wax is a polyethylene wax, and alternatively is a polyethylene wax having a melting point of less than 120° C., less than 95° C., or, alternatively, less than 85° C. In one embodiment, the was is a synthetic wax available as Cirebelle 305 from Cirebelle, South Africa.

Non-limiting examples of suitable silicone waxes are disclosed in U.S. Pat. Nos. 5,413,781 and 5,725,845, and further include alkylmethyl polysiloxanes, C10-C60 alkyl dimethicones, and mixtures thereof. Alternatively, the silicone wax may be a C16-C28 alkyl dimethicone wax. Other suitable silicone waxes include, but are not limited to stearoxydimethicone, behenoxy dimethicone, stearyl dimethicone, cetearyl dimethicone, cetyl dimethicone, and mixtures thereof.

E. Particulate Material

The composition of the present invention may comprise a particulate material. In one embodiment, the composition may comprise from about 0.001% to about 25%, from about 0.01% to about 15%, from about 0.01% to about 10%, or alternatively from about 0.1% to about 2% of a particulate material. Non-limiting examples of suitable particulate materials can be found in The Cosmetic, Toiletry, and Fragrance Association's *The International Cosmetic Ingredient Dictionary and Handbook*, 10$^{th}$ Ed., Gottschalck, T. E. and McEwen, Jr., Eds. (2004), p. 2728. Other suitable particulate materials include, but are not limited to almond meal, aluminum oxide, apricot seed powder, bismuth oxychloride, boron nitride, cellulose and cellulose derivatives, clay, calcium oxide, inorganic salts, for example salts of carbonates and chlorides, iron oxide, jojoba seed powder, loofah, mica, peach pit powder, pecan shell powder, polyethylene, polybutylene, polyisobutylene, polymethylstyrene, polypropylene, polystyrene, polyurethane, nylon, polytetrafluoroethylene, polyhalogenated olefins, pumice, rice bran, sericite, silk, synthetic hectorite, titanium dioxide, tricalcium phosphate, and mixtures thereof. Also useful are particles made from mixed polymers (e.g., copolymers, terpolymers, etc.), among such are polyethylene/polypropylene copolymer, polyethylene/propylene/isobutylene copolymer, polyethylene/styrene copolymer, and mixtures thereof. Typically, the polymeric and mixed polymeric particles are treated via an oxidation process, for example to destroy impurities. The polymeric and mixed polymeric particles can also optionally be cross linked with a variety of common crosslinking agents, non-limiting examples including butadiene, divinyl benzene, methylenebisacrylamide, allyl ethers of sucrose, allyl ethers of pentaerythritol, and mixtures thereof. Other examples of useful particles include waxes and resins such as paraffins, carnuba wax, ozekerite wax, candellila wax, and urea-formaldehyde resins. When such waxes and resins are used herein it is important that these materials are solids at ambient and skin temperatures.

Other examples of particulate materials useful in the present invention include colored and uncolored pigments, interference pigments, inorganic powders and organic powders other than those described above, composite powders, optical brightener particles, and mixtures thereof. The average size of such particulates may be from about 0.1 microns to about 100 microns. These particulates can, for example, be platelet shaped, spherical, elongated or needle-shaped, or irregularly shaped, surface coated or uncoated, porous or non-porous, charged or uncharged, and can be added to the current compositions as a powder or as a pre-dispersion. These particulate materials can be derived from natural and/or synthetic sources.

Also useful herein are interference pigments. Herein, "interference pigments" means thin, platelike layered particles having two or more layers of controlled thickness. The layers have different refractive indices that yield a characteristic reflected color from the interference of typically two, but occasionally more, light reflections, from different layers of the platelike particle. The most common examples of interference pigments are micas layered with about 50-300 nm films of $TiO_2$, $Fe_2O_3$, silica, tin oxide, and/or $Cr_2O_3$. Such pigments often are pearlescent. Pearlescent pigments reflect, refract and transmit light because of the transparency of pigment particles and the large difference in the refractive index of mica platelets and, for example, the titanium dioxide coating. Intereference pigments are available commercially from a wide variety of suppliers, for example, Rona (Timiron™ and Dichrona™), Presperse (Flonac™), Englehard (Duochrome™), Kobo (SK-45-R and SK-45-G), BASF (Sicopearls™) and Eckart (Prestige™) In one embodiment, the average diameter of the longest side of the individual particles of interference pigments is less than about 75 microns, and alternatively less than about 50 microns.

Other pigments useful in the present invention can provide color primarily through selective absorption of specific wavelengths of visible light, and include inorganic pigments, organic pigments and combinations thereof. Examples of such useful inorganic pigments include iron oxides, ferric ammonium ferrocyanide, manganese violet, ultramarine blue, and chromium oxide. Organic pigments can include natural colorants and synthetic monomeric and polymeric colorants. An example is phthalocyanine blue and green pigment. Also useful are lakes, primary FD&C or D&C lakes and blends thereof. Also useful are encapsulated soluble or insoluble dyes and other colorants. Inorganic white or uncolored pigments useful in the present invention, for example $TiO_2$, ZnO, or $ZrO_2$, are commercially available from a number of sources, for example, TRONOX $TiO_2$ series, SAT-T CR837, a rutile TiO2 (U.S. Cosmetics). Also suitable are charged dispersions of titanium dioxide, disclosed in U.S. Pat. No. 5,997,887, issued to Ha et al.

F. Thickening Agents

The compositions of the present invention may comprise from about 0.1% to about 5%, alternatively from about 0.1% to about 4%, and alternatively from about 0.25% to about 3%, of a thickening agent. Nonlimiting classes of thickening agents include but not limited to carboxylic acid polymers, polyacrylamide polymers, polysaccharides, sulfonated polymers, gums, copolymers thereof, hydrophobically modified derivatives thereof, and mixtures thereof.

G. Actives

The skin care composition of the present invention may comprise a safe and effective amount of one or more skin care active ("active") useful for regulating and/or improving skin condition. Suitable actives include, but are not limited to, vitamins, peptides, sugar amines, sunscreens, oil control agents, tanning actives, anti-acne actives, desquamation actives, anti-cellulite actives, chelating agents, skin lightening agents, flavonoids, protease inhibitors, non-vitamin antioxidants and radical scavengers, hair growth regulators, anti-wrinkle actives, anti-atrophy actives, minerals, phytosterols and/or plant hormones, tyrosinase inhibitors, anti-inflammatory agents, N-acyl amino acid compounds, antimicrobials, and antifungals. The skin care composition may comprise of the "Vitamins" means vitamins, pro-vitamins, and their salts, isomers and derivatives. Non-limiting examples of suitable vitamins include: vitamin B compounds (including B1 compounds, B2 compounds, B3 compounds such as niacinamide, niacinnicotinic acid, tocopheryl nicotinate, C1-C18 nicotinic acid esters, and nicotinyl alcohol; B5 compounds, such as panthenol or "pro-B5", pantothenic acid, pantothenyl; B6 compounds, such as pyroxidine, pyridoxal, pyridoxamine; carnitine, thiamine, riboflavin); vitamin A compounds, and all natural and/or synthetic analogs of Vitamin A, including retinoids, retinol, retinyl acetate, retinyl palmitate, retinoic acid, retinaldehyde, retinyl propionate, carotenoids (pro-vitamin A), and other compounds which possess the biological activity of Vitamin A; vitamin D compounds; vitamin K compounds; vitamin E compounds, or tocopherol, including tocopherol sorbate, tocopherol acetate, other esters of tocopherol and tocopheryl compounds; vitamin C compounds, including ascorbate, ascorbyl esters of fatty acids, and ascorbic acid derivatives, for example, ascorbyl phosphates such as magnesium ascorbyl phosphate and sodium ascorbyl phosphate, ascorbyl glucoside, and ascorbyl sorbate; and vitamin F compounds, such as saturated and/or unsaturated fatty acids.

"Peptide" refers to peptides containing ten or fewer amino acids, their derivatives, isomers, and complexes with other species such as metal ions (for example, copper, zinc, manganese, and magnesium). As used herein, peptide refers to both naturally occurring and synthesized peptides. In one embodiment, the peptides are di-, tri-, tetra-, penta-, and hexa-peptides, their salts, isomers, derivatives, and mixtures thereof. Suitable peptides include, but are not limited to, peptides derived from soy proteins, carnosine, palmitoyl-lysine-threonine (pal-KT) and palmitoyl-lysine-threonine-threonine-lysine-serine (pal-KTTKS, available in a composition known as MATRIXYL®), palmitoyl-glycine-glutamine-proline-arginine (pal-GQPR, available in a composition known as RIGIN®), these three being available from Sederma, France, acetyl-glutamate-glutamate-methionine-glutamine-arginine-arginine (Ac-EEMQRR; Argireline®), and Cu-histidine-glycine-glycine (Cu-HGG, also known as IAMIN®).

The compositions of the present invention may comprise a sugar amine, also known as amino sugars, and their salts, isomers, tautomers and derivatives. Sugar amines can be synthetic or natural in origin and can be used as pure compounds or as mixtures of compounds (e.g., extracts from natural sources or mixtures of synthetic materials). For example, glucosamine is generally found in many shellfish and can also be derived from fungal sources. Sugar amine compounds useful in the present invention include, for example, N-acetyl-glucosamine, and also those described in PCT Publication WO 02/076423 and U.S. Pat. No. 6,159,485, issued to Yu, et al.

The compositions of the present invention may comprise one or more sunscreen actives (or sunscreen agents) and/or ultraviolet light absorbers. Herein, suitable sunscreen actives include oil-soluble sunscreens, insoluble sunscreens, and water-soluble sunscreens. Non-limiting examples of suitable oil-soluble sunscreens are disclosed in The Cosmetic, Toiletry, and Fragrance Association's *The International Cosmetic Ingredient Dictionary and Handbook*, 10$^{th}$ Ed., Gottschalck, T. E. and McEwen, Jr., Eds. (2004), p. 2267 and pp. 2292-93 and include benzophenone-3, bis-ethylhexyloxyphenol methoxyphenyl triazine, butyl methoxydibenzoyl-methane, diethylamino hydroxy-benzoyl hexyl benzoate, drometrizole trisiloxane, ethylhexyl methoxy-cinnamate, ethylhexyl salicylate, ethylhexyl triazone, octocrylene, homosalate, polysilicone-15, and derivatives and mixtures thereof.

Non-limiting examples of suitable insoluble sunscreens include methylene bis-benzotriazolyl tetramethylbutyl-phenol, titanium dioxide, zinc cerium oxide, zinc oxide, and derivatives and mixtures thereof.

Non-limiting examples of suitable water-soluble sunscreens include phenylbenzimidazole sulfonic acid (PBSA), terephthalylidene dicamphor sulfonic acid, (Mexoryl™ SX), benzophenone-4, benzophenone-5, benzylidene camphor sulfonic acid, cinnamidopropyltrimonium chloride, methoxycinnamido-propyl ethyldimonium chloride ether, disodium bisethylphenyl triaminotriazine stilbenedisulfonate, disodium distyrylbiphenyl disulfonate, disodium phenyl dibenzimidazole tetrasulfonate, methoxycinnamido-propyl hydroxysultaine, methoxycinnamido-propyl laurdimonium tosylate, PEG-25 PABA (p-aminobenzoic acid), polyquaternium-59, TEA-salicylate, and salts, derivatives and mixtures thereof.

The compositions of the present invention may comprise one or more compounds for regulating the production of skin oil, or sebum, and for improving the appearance of oily skin. Examples of suitable oil control agents include salicylic acid, dehydroacetic acid, benzoyl peroxide, vitamin B3 compounds (for example, niacinamide or tocopheryl nicotinate), their isomers, esters, salts and derivatives, and mixtures thereof.

The compositions of the present invention may comprise a skin lightening agent including kojic acid, arbutin, tranexamic acid, ascorbic acid and derivatives (e.g., magnesium ascorbyl phosphate or sodium ascorbyl phosphate or other salts of ascorbyl phosphate), ascorbyl glucoside, undecylenoyl phenylalanine (Sepiwhite® from SEPPIC), aloesin, Actiwhite® (Cognis), and Emblica® (Rona).

The compositions of the present invention may comprise protease inhibitors including, but are not limited to, hexamidine (including salts and derivates thereof), vanillin acetate, menthyl anthranilate, soybean trypsin inhibitor, Bowman-Birk inhibitor, and mixtures thereof.

The compositions of the present invention may other optional components such as anti-acne actives, desquamation actives, anti-cellulite agents, chelating agents, flavonoids, tanning active, non-vitamin antioxidants and radical scavengers, hair growth regulators, anti-wrinkle actives, anti-atrophy actives, minerals, phytosterols and/or plant hormones, tyrosinase inhibitors, anti-inflammatory agents, N-acyl amino acid compounds, antimicrobial or antifungal actives, and other useful skin care actives, which are described in further detail in U.S. application publication No. US2006/0275237A1 and US2004/0175347A1.

Antiperspirant actives may include astringent metallic salts, especially inorganic and organic salts of aluminum, zirconium and zinc, as well as mixtures thereof. Particular antiperspirant active examples include, but are not limited to, aluminum-containing and/or zirconium-containing salts or materials, such as aluminum halides, aluminum chlorohydrate, aluminum hydroxyhalides, zirconyl oxyhalides, zirconyl hydroxyhalides, and mixtures thereof.

Deodorant actives may be selected from the group consisting of antimicrobial agents (e.g., bacteriocides, fungicides), malodor-absorbing material, and combinations thereof. For example, antimicrobial agents may comprise cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof.

In certain embodiments of the present invention, the personal care composition is substantially free of or contains no antiperspirant actives and deodorant actives. In specific embodiments, the personal care composition comprises no more than about 0.01% or, alternatively, no more than about 0.001% of antiperspirant actives and deodorant actives II. Dispensing Container The personal care product of the present invention further comprises a dispensing container that may contain and dispense the personal care composition. As presented in the background, it is desirable to provide a personal care composition having a solid character but still providing good rub-in and skin absorbency characteristics. The dispensing containers of the present invention preserve a portion of the pre-dispense G' of the personal care composition. More specifically, the dispensing containers dispense the personal care composition which exhibits a post-dispense G'. The term "post-dispense G'" refers to the G' of the personal care composition after having been dispensed from the dispensing container as measured according to the test method provided below. The post-dispense personal care composition exhibits a post-dispense G'. The percentage of G' preserved by the personal care product may be calculated according to the following formula:

$$G' \text{ preservation percentage} = \left[\left(\frac{\text{Post-Dispense } G'}{\text{Pre-Dispense } G'}\right) \times 100\right]$$

The personal care product of the present invention exhibits a G' preservation percentage of at least 10%. In other embodiments, the personal care product of the present invention exhibits a G' preservation percentage of at least about 20%, about 30%, or, alternatively, about 45%. In another embodiment, the personal care product of the present invention may exhibit a G' preservation percentage of at least about 80% or at least about 85%. In certain embodiments, the personal care product exhibits a G' preservation percentage between a lower limit of about 20%, about 25%, or, alternatively, about 35% and an upper limit of about 85%, 80%, or, alternatively, about 50%.

Figure 1B:
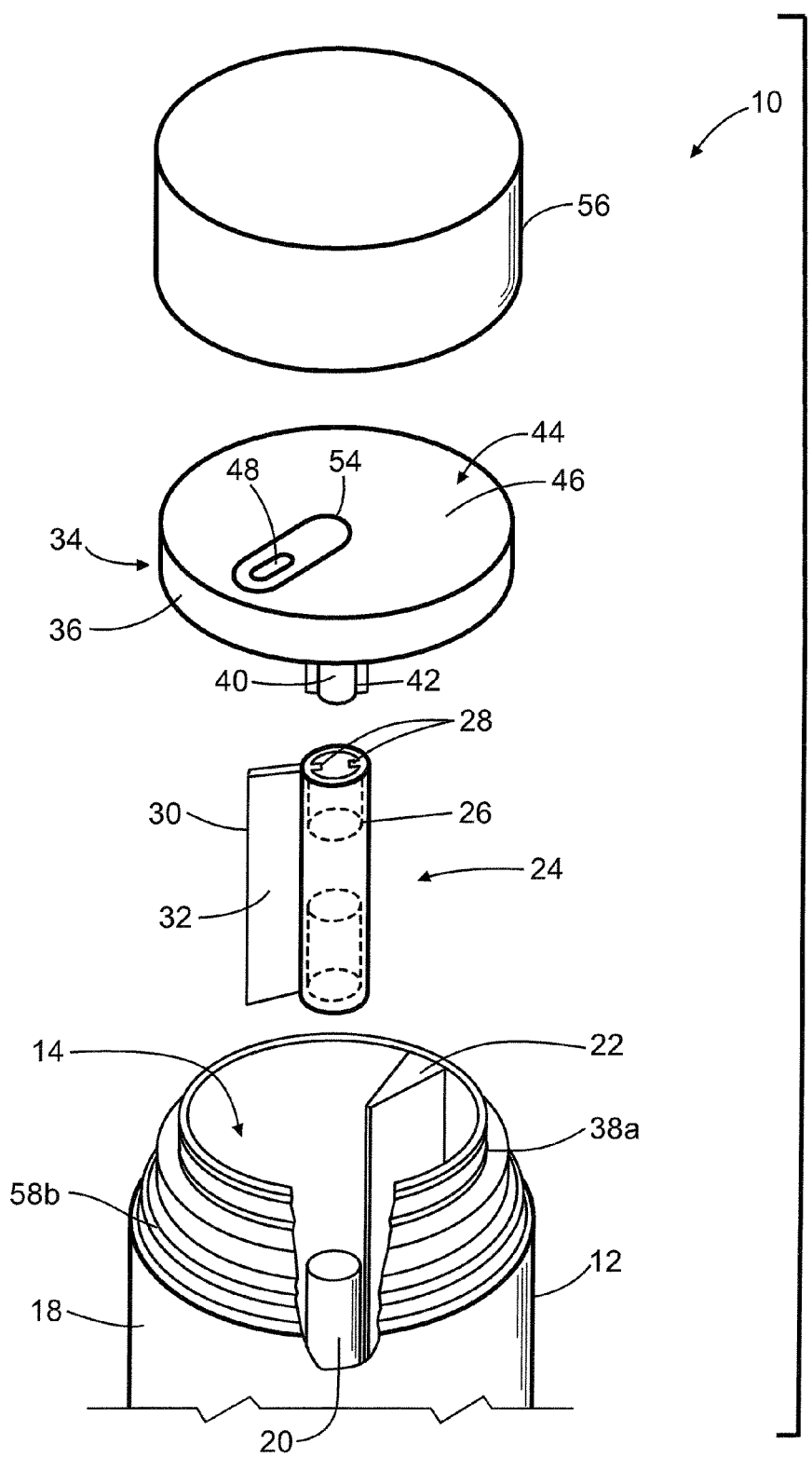
FIG. 1B is an exploded of the dispensing container of FIG. 1A with a partial cut-away view in order to show hidden structure.
Figure 1C:
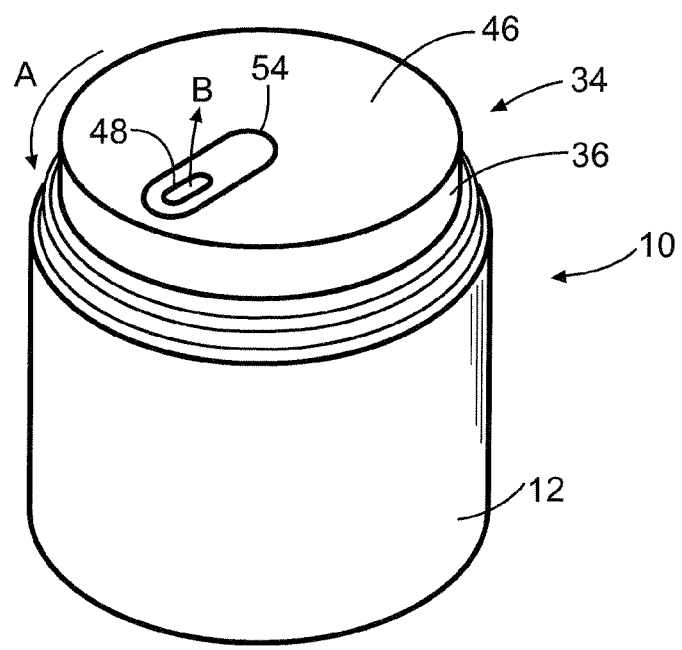
FIG. 1C is a perspective view of the dispensing container of FIG. 1A (with the optional overcap removed).
Figure 2A:
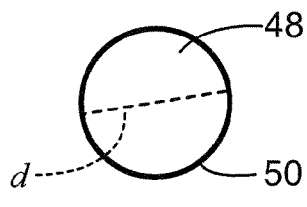
FIGS. 2A-F depicts a variety of orifice shapes.
Figure 2B:
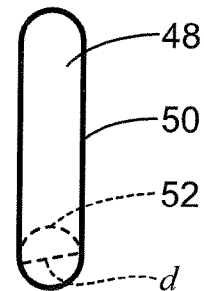
Figure 2C:
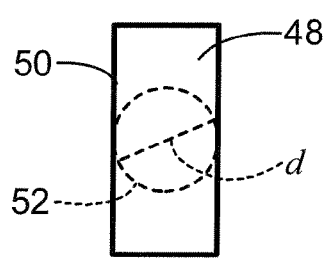
Figure 2D:
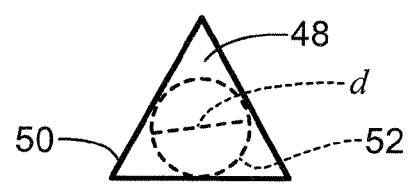
Figure 2E:
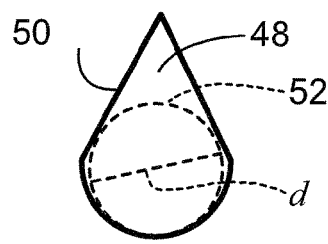
Figure 2F:
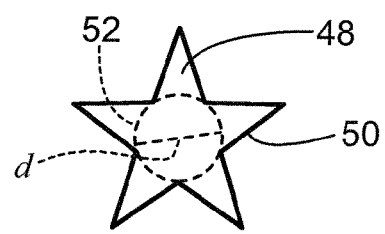

A suitable embodiment of the dispensing container is shown in FIGS. 1A-C. FIG. 1A is a cross-sectional view of an approximately bisected dispensing container. FIG. 1B is an exploded of the dispensing container with a partial cut-away view in order to show hidden structure. FIG. 1C is a perspective view of the dispensing container (with the optional overcap removed). The dispensing container 10 comprises a container body 12 having a storage void 14 therein. The storage void 14 is the portion of the dispensing container 10 wherein the personal care composition is disposed. The container body 12 may be constructed from any suitable materials such as rigid plastic. The container body 12 and storage void 14 may be any suitable size or shape sufficient to store a bulk quantity of personal care composition. The storage void 14 may be sized to storage a sufficient quantity of personal care composition for multiple applications (i.e., the entire bulk quantity of personal care composition is not dispensed in a single use). The container body 12 and storage void 14 are shown as being substantially cylindrical in shape. The container body 12 may have a bottom wall 16 and a side wall 18. The construction of the container body 12 is not limited. For example, the bottom wall 16 and side wall 18 may be hollow or solid (i.e., not hollow). The container body 12 may comprise a translucent region allowing visual inspection of the personal care composition within the storage void 14. The translucent region may serve as a meter for visually determining the amount of personal care composition remaining in the dispensing container 10. The translucent region may be translucent or transparent. In certain embodiments, the container body 12 may be substantially translucent. The container body 12 further comprises a support pillar 20. The support pillar 20 may be cylindrical in shape. The support pillar 20 may rise from approximately the center of the bottom wall 16 of the container body 12. The container body 12 may include a fixed partition 22 extending inwardly from the sidewall 18 toward the support pillar 20.

The dispensing container 10 may further comprise a movable partition 24. The movable partition 24 is at least partially disposed within the storage void 14. The movable partition 24 may comprise an axial member 26. The axial member 26 may be a tube-like member that may be fitted onto the support pillar 20. The axial member 26 may be disposed such that it may rotate about the support pillar 20. The axial member 26 may be proximate to or in contact with the fixed partition 22. The axial member 26 may comprise one or more engaging structures 28 (shown in FIG. 1B). The movable partition 24 may also include a partition plate 30. The partition plate 30 is shown in FIG. 1B as being disposed radially from the axial member 26. The outer edges of the partition plate 30 may be proximate to or in contact with the bottom wall 16 and the side wall 18. The partition plate 30 may include a contacting surface 32 that contacts or may be brought into contact with the personal care composition during use of the dispensing container 10. The movable partition 24, the bottom wall 16, the side wall 18, and the fixed partition 22 define the volume of the storage void 14 within which the personal care composition is disposed.

The dispensing container 10 may further comprise a drive mechanism 34. The drive mechanism 34 acts upon and moves the movable partition 24. The drive mechanism 34 generally moves the movable partition 24 in contact with the personal care composition. The movable partition 24 may then apply a force upon the personal care composition. In the embodiment depicted, the drive mechanism comprises a hand wheel 36. The hand wheel 36 may be rotatably joined to the container body 12 such as by annular protrusion 38a extending from the container body and mated annular recess 38b within the hand wheel 36. The drive mechanism 34 comprises an engaging post 40 extending approximately from the center of the hand wheel 36. The engaging post 40 connects the hand wheel 36 to the movable partition 24 allowing the movement of the hand wheel 36 to be conveyed to the movable partition 24. The engaging post 40 may be positioned within the hollow interior of the axial member 26. The engaging post 40 and axial member 26 may be mechanically linked by one or more longitudinally extending slots 42 within the engaging post 40 that mate with the engaging structures 28 (e.g., longitudinally extending ribs) of the axial member 26. In the embodiment shown in FIGS. 1A-C, the drive mechanism 34 may define the upper boundary of the storage void 14.

The dispensing container 10 comprises a dispensing plate 44 onto which the personal care composition may be dispensed. The dispensing plate 44 comprises a dispensing surface 46 that may define the uppermost surface of the dispensing container 10. The dispensing plate 44 comprises an orifice 48 through which the personal care composition is dispensed. During use of the dispensing container 10, as shown in FIG. 1C, the drive mechanism 34 is initiated by a user (e.g., by turning the hand wheel 36 such as shown by directional arrow A) which moves the movable partition 24 in a rotational path in contact with the personal care composition. The movable partition 24 applies a force upon the personal care composition which causes a portion of the personal care composition to move from the storage void 14, through the orifice 48, and onto the dispensing plate 44 (as shown by directional arrow B). In the embodiment shown in FIGS. 1A-C the dispensing plate 44 is integral with the drive mechanism 34 (specifically, the hand wheel 36). In a particular embodiment, the dispensing surface 46 is non-convex (i.e., concave or flat). The orifice 48 is disposed through the dispensing plate 44 and serves as the passage through which the personal care composition is dispensed. The location of the orifice 48 in the dispensing plate 44 is not limited and, in an exemplary embodiment, is shown as being disposed nearer to the periphery than to the center of the dispensing plate 44. While a single orifice 48 is shown in FIGS. 1A-C, the dispensing container may comprise a plurality of orifices.

In certain embodiments, the surface area and/or the shape (e.g., non-convex) of the dispensing surface 46 are configured to hinder the use of the dispensing container 10 as an applicator (i.e., hinder directly applying the dispensing surface 46 of the dispensing container 10 to the skin targeted for treatment, typically on the face). In some embodiments, the dispensing surface 46 may have a measurable surface area of greater than about 12 cm$^2$, 20 cm$^2$, about 25 cm$^2$, or, alternatively, about 30 cm$^2$. In some embodiments, the orifice 48 has an open area that covers no more than about 15%, about 10%, or, alternatively, about 5% of the surface area of the dispensing surface 46. The surface area of the dispensing surface 46 and the open area of the orifice 48 may be calculated according conventional mathematical techniques. Alternately, the surface area of the dispensing surface 46 and the open area of the orifice 48 may be measured with the assistance of computer aided imaging software such as Solidworks available from SolidWorks Corp., Concord, Mass. or Pro/Engineer available from Parametric Technology Corp., Needham, Mass.

While not wishing to be bound by theory, it is believed that the shape of the orifice 48 may impact the post-dispense G' of the personal care composition (and consequently the G' preservation percentage of the personal care product) during dispensation from the dispensing container 10, as well as other embodiments of the dispensing container having an orifice. It is believed that the orifice 48 shape must balance the maximum linear dimension of the orifice 48 (i.e., the longest straight line that may be drawn within the orifice) and the open area of the orifice 48. The balancing of factors is characterized by an inscribed circle diameter ("ICD"). Nearly all shapes allow for a circle to be inscribed within the shape. The inscribed circle is the largest diameter circle that may be drawn within the shape of the orifice 48 so that the circle lies entirely within the boundary of the orifice. FIGS. 2A-F depicts a variety of orifice shapes (e.g., circle, round-ended slot, rectangle, triangle, teardrop, and star, respectively). Each orifice 48 has a boundary 50 that defines the shape. An inscribed circle 52 is shown by broken lines in each figure (except for FIG. 2A wherein the inscribed circle would be the same as the boundary 50). Each inscribed circle 52 has a measurable diameter d. The diameter d is the inscribed circle diameter. In certain embodiments, the orifice 48 has an inscribed circle diameter of at least about 1 mm, at least about 2 mm, at least about 4 mm, at least about 6 mm or, alternatively, at least about 8 mm. In certain embodiments, the inscribed circle diameter may be less than about 12 mm in order to maintain the sanitary condition of the personal care composition within the storage void 14 (i.e., the orifice 48 may be sized such that a user generally can not access the storage void 14 with the user's finger). The inscription of a circle 52 within the orifice 48 shape and calculation of the diameter of the inscribed circle 52 may be done by conventional mathematical techniques; however, it is preferred that this work be done with the assistance of computer aided imaging software such as SolidWorks or Pro/Engineer.

The dispensing plate 44 may further comprise a finger divot 54. The finger divot 54 is a recess in the dispensing surface 46 of the dispensing plate 44. The finger divot 54 may communicate to the user the location where the personal care composition may be collected from the dispensing surface 46. The finger divot 54 is shown in FIGS. 1A-C as having an elliptical shape; however, the shape of the finger divot 54 is not limited. The finger divot 54 may have a concave surface. The finger divot 54 may be proximate to the orifice 48. In certain embodiments such as shown in FIGS. 1A-C, the orifice 48 maybe be disposed within the finger divot 54.

The dispensing container 10 may further comprise an overcap 56. The overcap 56 may be removably joined to the container body 12. The overcap 56 may also be replaceably joined to the container body 12. In one embodiment, as shown in FIG. 1A, the overcap 56 includes threads 58a that may be mated with threads 58b of the container body 12. In other embodiments, the overcap 56 may be sized to snuggly fit over a portion of the container body 12 without the need for mating members between the overcap 56 and container body 12. The overcap 56 may cover the orifice 48 when the overcap 56 is joined to the container body 12 such that the orifice 48 is not exposed.

Figure 3:
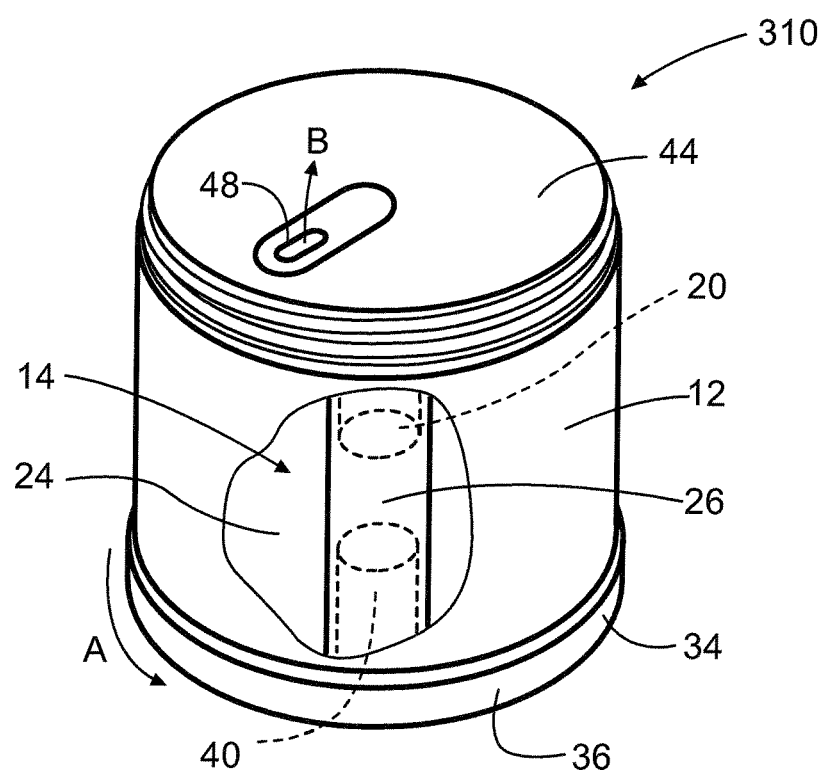
FIG. 3 is a perspective view of an embodiment of a dispensing container.

FIGS. 1A-C depict one embodiment of the dispensing container. FIG. 3 is a perspective view of a variant of the dispensing container provided in FIGS. 1A-C. The dispensing container 310 has many of the same structures as the dispensing container 10 of FIG. 1A-C. The dispensing container 310 differs, in at least one respect, by having the dispensing plate 44 as a structure discrete from the drive mechanism 34. As provided in FIG. 3, the drive mechanism 34 is a hand wheel 36 disposed on opposing end of the container body 12 away from the dispensing plate 44. As should be readily appreciated, dissociating the drive mechanism 34 and the dispensing plate 44 may require other structural modifications. The drive mechanism 34 may function as the bottom wall of the container body 12. The dispensing plate 44 may be integral to the container body 12 or may be a discrete member joined to the container body 12. As shown in cutaway, the support pillar 20 may extend from the bottom surface of the dispensing plate 44 and into the storage void 14. The drive mechanism 34 comprises an engaging post 40 extending approximately from the center of the hand wheel 36. The engaging post 40 connects the hand wheel 36 to the movable partition 24 allowing the movement of the hand wheel 36 to be conveyed to the movable partition 24. As shown, the engaging post 40 may be positioned within the hollow interior of the axial member 26 of the movable partition. The dispensing container 310 is operated by the user by turning the hand wheel 36 (shown as directional arrow A) which moves the movable partition 24 in a rotational path in contact with the personal care composition. The movable partition 24 applies a force upon the personal care composition which causes a portion of the personal care composition to move from the storage void 14, through the orifice 48, and onto the dispensing plate 44 (shown as directional arrow B).

Other embodiments of the dispensing container 410 are provided in International Publication WO 2006/075484.

Figure 4A:
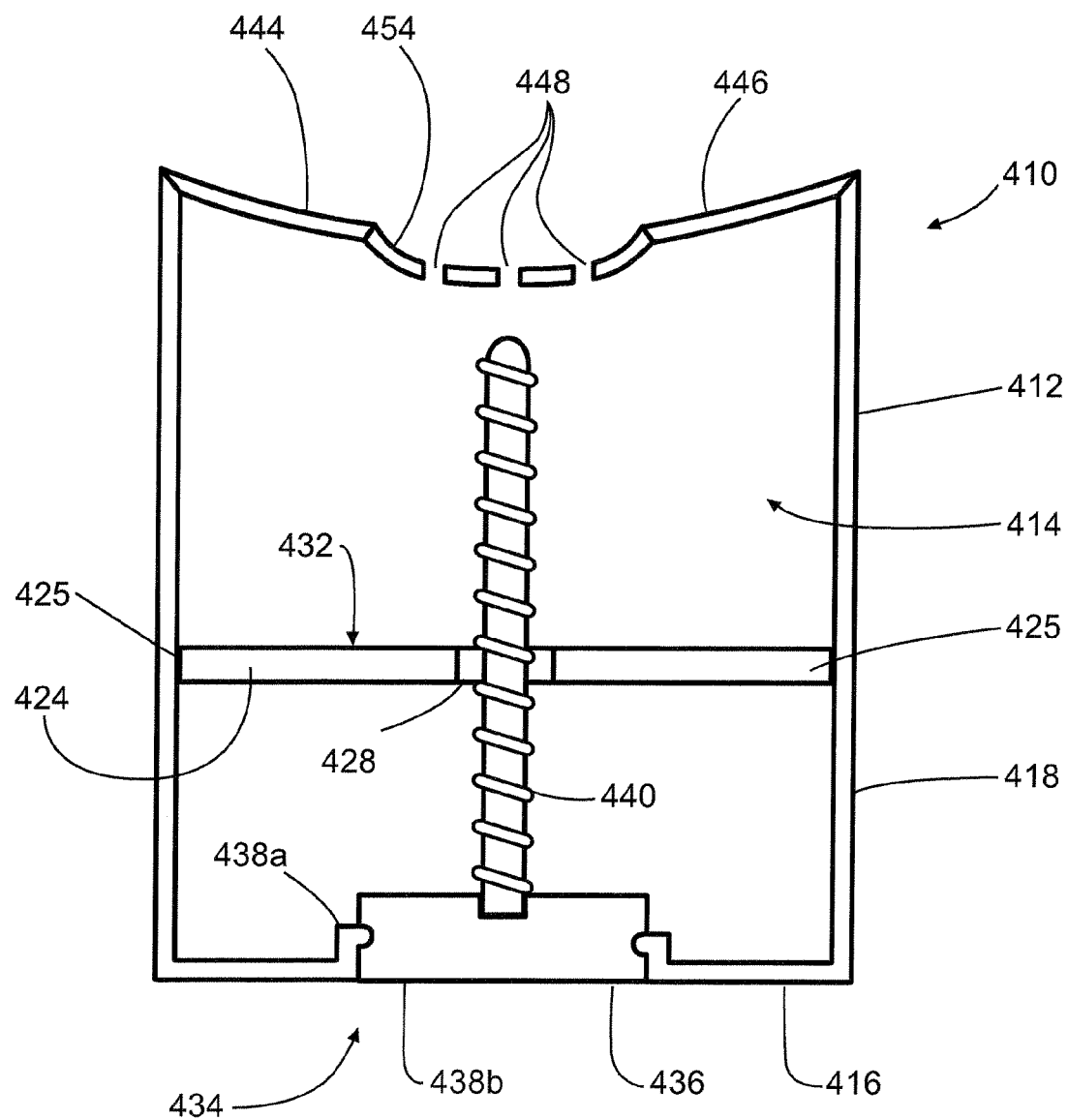
FIG. 4A is a cross-sectional view of an embodiment of a dispensing container.
Figure 4B:
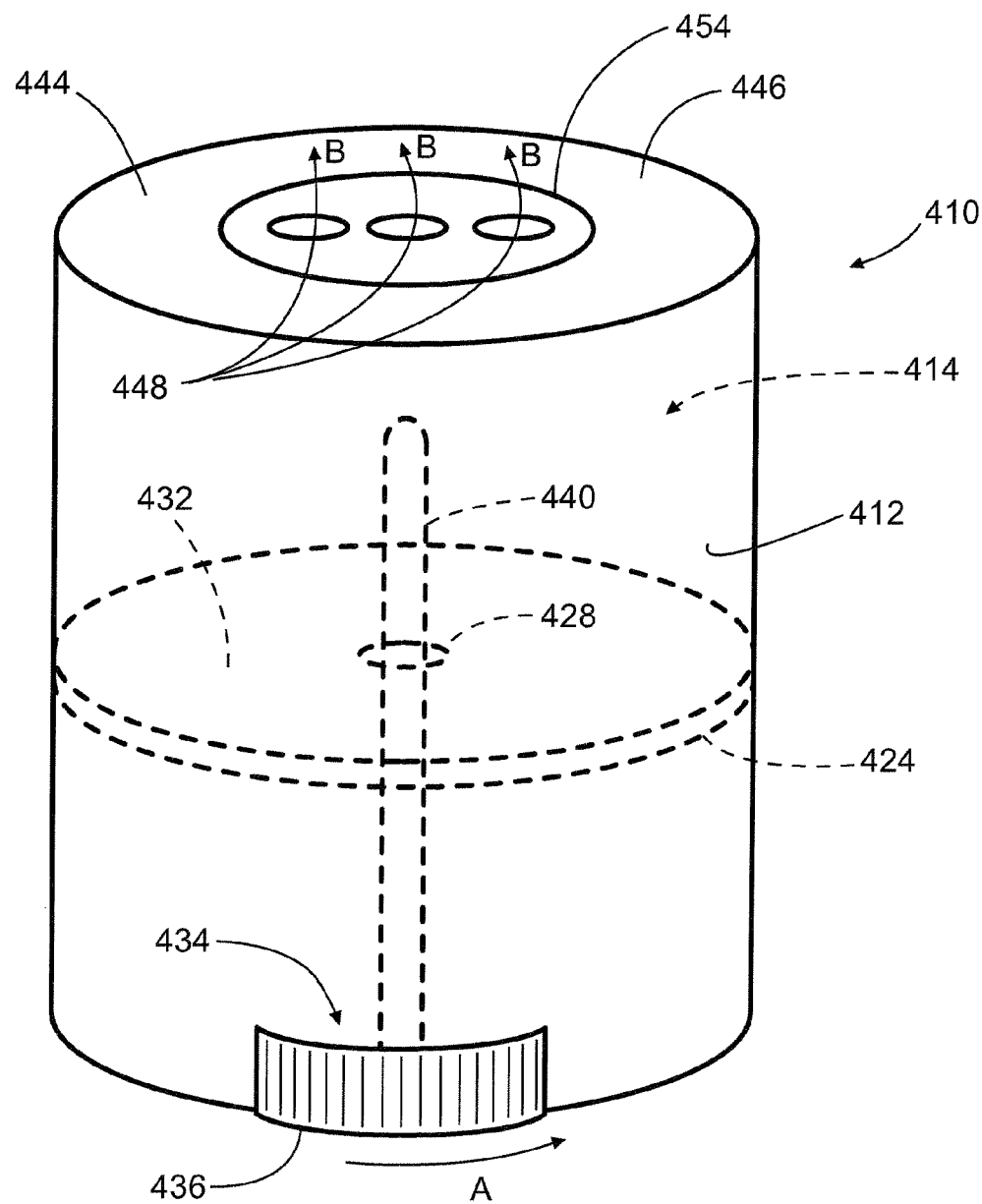
FIG. 4B is a perspective view of the dispensing container of FIG. 4A.

FIGS. 4A-B depict another embodiment of the dispensing container. FIG. 4A is a cross-sectional view of an approximately bisected dispensing container 410. FIG. 4B is a perspective view of the dispensing container 410 in operation. The dispensing container 410 comprises a container body 412 having a storage void 414 therein. The container body 412 and storage void 414 may be any suitable size or shape sufficient to store a bulk quantity of personal care composition. The storage void 414 may be sized to storage a sufficient quantity of personal care composition for multiple applications (i.e., the entire bulk quantity of personal care composition is not dispensed in a single use). The container body 412 and storage void 414 are shown as being substantially cylindrical in shape with an elliptical base. The container body 412 may have a bottom wall 416 and a side wall 418. The dispensing container 410 comprises a container body 412 having a storage void 414 therein.

The dispensing container 410 may comprise a movable partition 424. The movable partition 424 is at least partially disposed within the storage void 414. The movable partition 424 has an outer edge 425 proximate to or in contact with side wall 418. The movable partition 424 may include a contacting surface 432 that contacts or may be brought into contact with the personal care composition during use of the dispensing container 410. The movable partition 424 may include an engaging structure 428 such as a threaded opening in the movable partition 424.

The dispensing container 410 may further comprise a drive mechanism 434. The drive mechanism 434 acts upon and moves the movable partition 424. The drive mechanism 434 generally moves the movable partition 424 in contact with the personal care composition. In the embodiment depicted, the drive mechanism 434 is a screw lift. The drive mechanism 434 comprises a hand wheel 436. The hand wheel 436 is rotatably joined to the container body 414 such as by mating an annular protrusion 438a extending from the container body 412 with an annular recess 438b within the hand wheel 436. The drive mechanism 434 comprises a feed screw 440 extending approximately from the center of the hand wheel 436. The feed screw 440 engages the movable partition 424 through the threaded opening of the engaging structure 428. The feed screw 440 is joined to the hand wheel 436 such that rotational motion of the hand wheel 436 may be conveyed to feed screw 440. The rotational motion of the feed screw 440 advances the movable partition in a linear path within the storage void 414.

The dispensing container 410 comprises a dispensing plate 444 onto which the personal care composition may be dispensed. The dispensing plate 444 comprises a dispensing surface 446 that may define the uppermost surface of the dispensing container 410. The movable partition 424, the side wall 418 of the container body 412, and the dispensing plate 444 define a storage region within the storage void 414 within which the personal care composition is disposed. The dispensing plate 444 may be a discrete element joined to the container body 412 or may be integral to the container body 412. The dispensing plate 444 comprises a plurality of orifices 448 through which the personal care composition is dispensed. As shown in FIG. 4B, during use of the dispensing container 410, the drive mechanism 434 is initiated by a user (e.g., by turning the hand wheel 436 in direction A) which moves the movable partition 424 in a linear path in contact with the personal care composition. The movable partition 424 applies a force upon the personal care composition which causes a portion of the personal care composition to move from the storage void 414, through the orifices 448, and onto the dispensing plate 444 (as shown by directional arrows B). The dispensing surface 446 may have a measurable surface area of greater than about 12 $cm^2$, 20 $cm^2$, about 25 $cm^2$, or, alternatively, about 30 $cm^2$. In some embodiments, the orifice 448 has an open area that covers no more than about 15%, about 10%, or, alternatively, about 5% of the surface area of the dispensing surface 446. The dispensing plate 44 may further comprise a finger divot 454. The finger divot 454 is shown as a concave recess in the dispensing surface 446. The orifices 448 are shown as being disposed within the finger divot 454.

The dispensing container 410 may further comprise an overcap; however, an overcap is not shown in this embodiment.

Figure 5:
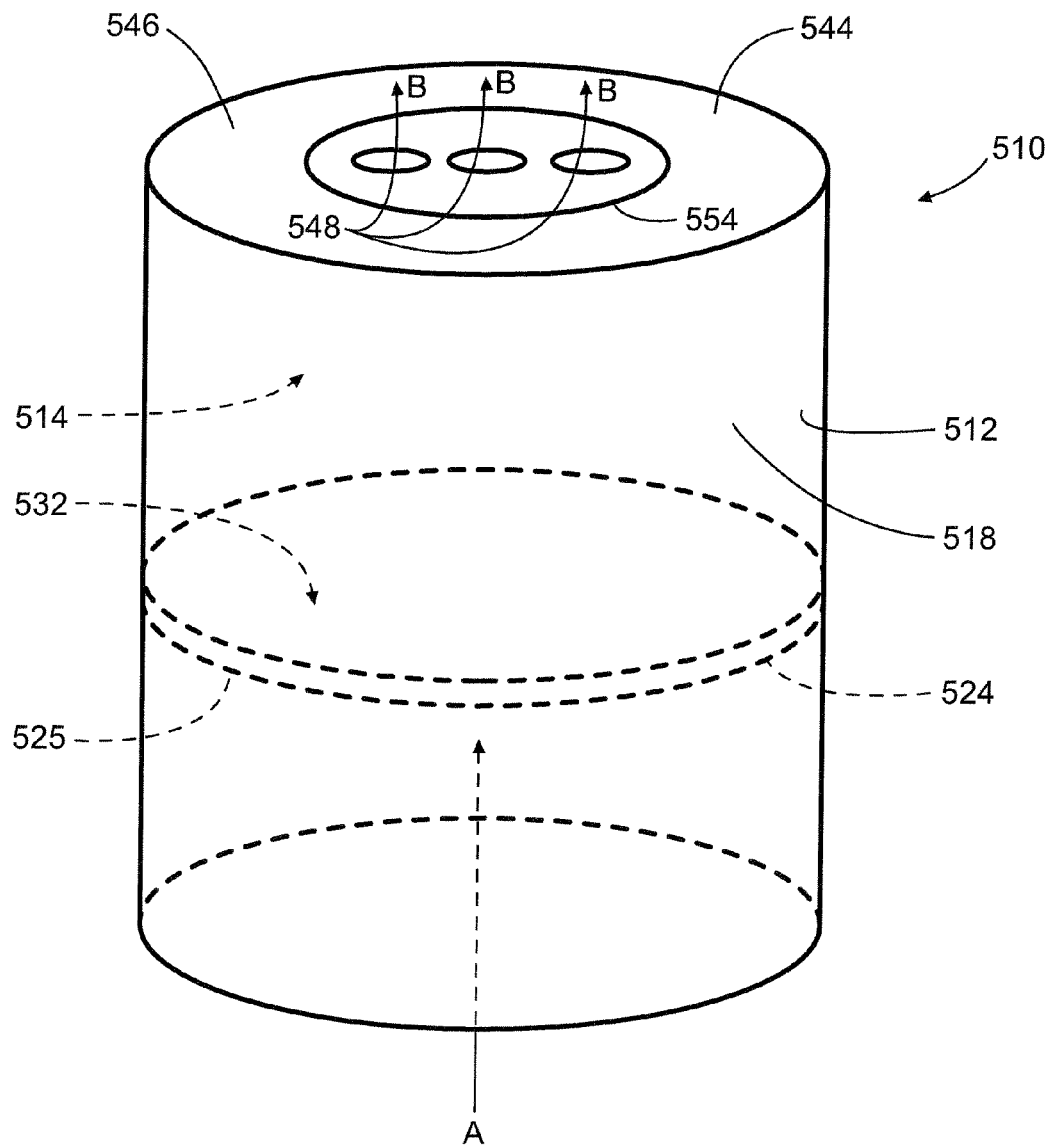
FIG. 5 is a perspective view of another embodiment of the dispensing container.

FIG. 5 depicts another embodiment of the dispensing container 510. The dispensing container 510 is similar to dispensing container 410; however, dispensing container 510 omits a drive mechanism. The dispensing container 510 comprises a container body 512 having a storage void 514 therein. The container body 512 may have a side wall 518 but is substantially open on the bottom surface. The dispensing container 510 may comprise a movable partition 524. The movable partition 524 is at least partially disposed within the storage void 514. The movable partition 524 has an outer edge 525 proximate to or in contact with side wall 518. The movable partition 524 may include a contacting surface 532 that contacts or may be brought into contact with the personal care composition during use of the dispensing container 510.

The dispensing container 510 comprises a dispensing plate 544 onto which the personal care composition may be dispensed. The dispensing plate 544 comprises a dispensing surface 546 that may define the uppermost surface of the dispensing container 510. The movable partition 524, the side wall 518 of the container body 512, and the dispensing plate 544 define a storage region within the storage void 514 within which the personal care composition is disposed. The dispensing plate 544 comprises a plurality of orifices 448 through which the personal care composition is dispensed. The dispensing plate 544 may further comprise a finger divot 554. During use of the dispensing container 510, a user applies a force (directional line A) to the movable partition 524 (e.g., user pushes the movable partition with her finger(s)). The movable partition 524 applies a force upon the personal care composition which causes a portion of the personal care composition to move from the storage void 514, through the orifices 548, and onto the dispensing plate 544 (as shown by directional arrows B).

The elements and description of any one embodiment are taken as exemplary and are equally applicable to other embodiments and equivalents that may not expressly recite such elements and description. Furthermore, it should be recognized that elements shown as discrete may be configured, in other embodiments, as integral and integral elements may be configured as discrete.

II. Methods of Use

The present invention further describes a method of regulating and/or improving the condition of mammalian skin. The method comprises the steps of dispensing the personal care composition from the dispensing container and of topically applying to mammalian skin a personal care composition described herein. Alternatively, the method may comprise the step of applying the composition described herein to insult-affected keratinous tissue, to regulate and/or improve the condition of such tissue, and/or to provide relief from the effects of the insult.

The composition may be applied to any keratinous tissue, including keratinous tissue in need of one or more benefits. Benefits include regulating and/or improving the condition of keratinous tissue, non-limiting examples of which include reducing the appearance of wrinkles, reducing the appearance of deep lines, reducing the appearance of fine lines, reducing the appearance of large pores, reducing the thickness of keratinous tissue, increasing the convolution of the dermal-epidermal border, increasing elasticity, reducing the appearance of cellulite, reducing the appearance of discoloration, reducing the appearance of hyperpigmentation, reducing the appearance of under-eye circles, reducing the appearance of sallowness, and combinations thereof. Alternatively, the benefit may include reducing wrinkles, reducing deep lines, reducing fine lines, reducing large pores, reducing cellulite, reducing hyperpigmentation, reducing undereye circles, reducing puffiness, and combinations thereof.

The composition may be applied by a variety of means, including by rubbing, wiping or dabbing with hands or fingers. The composition may be applied by way of an implement and/or delivery enhancement device. Non-limiting examples of implements include a sponge or sponge-tipped applicator, a swab (for example, a cotton-tipped swab), a brush, a wipe, and combinations thereof. When using an implement, a suitable method comprises the steps of dispensing the personal care composition from the dispensing container, transferring the personal care composition to the implement, and topically applying to mammalian skin the personal care composition from the implement. Non-limiting examples of delivery enhancement devices include mechanical, electrical, ultrasonic and/or other energy devices.

The amount of the composition applied, the frequency of application and the period of use will vary widely depending upon the level of components of a given composition and the level of regulation desired. For example, from about 0.1 mg composition/cm$^2$ to about 50 mg composition/cm$^2$, and alternatively about 2 mg composition/cm$^2$ of keratinous tissue may be applied. In one embodiment, the composition is applied at least once daily. The composition further may be applied as part of a treatment regimen, for example, once daily for 30 consecutive days, alternatively for 14 consecutive days, alternatively for 7 consecutive days and alternatively for 2 consecutive days.

Examples

Examples 1-3 are non-limiting examples of compositions that may be applied to keratinous tissue. Examples 1 and 2 are within the scope of the present invention. Example 3 is a comparative example in the form of a conventional skin care lotion. The examples provided herein are not to be read as limiting; given the disclosure provided herein, one skilled in the art would appreciate that the examples may further comprise one or more other skin care actives.

|  | Example 1 | Example 2 | Example 3 |
|---|---|---|---|
| PHASE A |  |  |  |
| DC-9040 *1 | 5.10 | 5.10 | 13.5 |
| Dimethicone | 4.10 | 4.10 | — |
| Polymethylsilsesquioxane *2 | 4.10 | 4.10 | 7.5 |
| Cyclomethicone | 11.40 | 11.90 | 23.5 |
| KSG-210 *3 | 5.40 | 5.40 | 2.5 |
| Polyethylene wax *4 | 2.05 | — | — |
| DC-2503 Cosmetic Wax *5 | 3.77 | — | — |
| Cirebelle 305 *6 | — | 5.30 | — |
| Abil EM97 *7 | — | — | 0.45 |
| KF 6017 *8 | — | — | 0.375 |
| Cetyl Ricinoleate | — | — | 0.25 |
| Hydrophobically modified TiO2 Coated Mica *9 | 1.00 | 1.00 | — |
| Fragrance | 0.10 | 0.10 | 0.10 |
| PHASE B |  |  |  |
| Glycerin | 10.00 | 10.00 | 10.00 |
| Panthenol | 0.5 | 0.5 | 1.00 |
| Pentylene Glycol | 3.00 | 3.00 | — |
| Propylene Glycol | — | — | 1.00 |
| Butylene Glycol | — | — | 1.00 |
| Tocopherol Acetate | — | — | 0.50 |
| N-Acetyl Glucosamine | 0.50 | 0.50 | — |
| Hexamididine Diisethanoate *10 | 0.10 | 0.10 | — |
| Niacinamide | 5.00 | 5.00 | 4.00 |
| Methylparaben | 0.20 | 0.20 | 0.10 |
| Ethylparaben | 0.05 | 0.05 | 0.10 |
| Benzyl Alcohol | 0.25 | 0.25 | 0.50 |
| Propyl Paraben | — | — | 0.10 |
| Disodium EDTA | — | — | 0.10 |
| Sodium Chloride | 0.50 | 0.50 | — |
| Water | q.s to 100 | q.s to 100 | q.s to 100 |

*1 12.5% Dimethicone Crosspolymer in Cyclopentasiloxane. Available from Dow Corning
*2 E.g.,Tospearl 145A or Tospearl 2000. Available from GE Toshiba Silicone
*3 25% Dimethicone PEG-10/15 Crosspolymer in Dimethicone. Available from Shin-Etsu
*4 Jeenate 3H polyethylene wax. Available from Jeen
*5 Stearyl Dimethicone. Available from Dow Corning.
*6 Synthetic wax. Available from Cirebelle.
*7 Bis-PEG/PPG-14/14 Dimethicone. Available from Degussa
*8 PEG-10 Dimethicone. Available from Shin-Etsu.
*9 KTZ Fine TiO$_2$ coated Mica - MS6. Available from Kobo.
*10 Hexamidine diisethionate, availabile from Laboratoires Serobiologiques.

For examples 1 and 2, combine the ingredients of Phase A in a suitable container. In a separate suitable container, combine the ingredients of Phase B. Heat each phase to 75-80° C. while mixing each phase using a suitable mixer (e.g., Anchor blade, propeller blade) until each reaches temperature and is homogenous. Slowly add Phase B to Phase A while continuing to mix Phase A. Continue mixing until batch is uniform. Homogenize product with Ultra-Turrax homogenizer (IKA, Inc) or equivalent and pour product into suitable containers at 75-80° C. Store the containers at room temperature without disturbing for at least 12 hours.

For example 3, in a suitable container, combine the ingredients of Phase A and mix with a suitable mixer until homogenous. In a separate container, combine the ingredients of Phase B and mix until homogenous. Slowly add Phase B to Phase A while continuing to mix Phase A. Continue mixing until batch is uniform. Homogenize product with Ultra-Turrax homogenizer (IKA, Inc) or equivalent and pour product into suitable containers.

Containers A-E are non-limiting examples of containers. Container A is a standard jar with a lid. Container A does not fall within the present invention since it is not a dispensing container. Container A is used to show the pre-dispense G' for each of the skin care composition examples.

Container B is a dispensing container substantially similar to that of FIGS. 1A-C as described above. The dispensing container comprises a storage void having an available volume (i.e., volume that may contain the skin care composition) of about 75 cm$^3$. The storage void is substantially cylindrical with the approximate dimensions of 6.8 cm in diameter and 5.3 cm in depth. The dispensing container comprises a movable partition having a contacting surface with a surface area of about 9.6 cm². The dispensing container comprises a concave dispensing plate with a surface area of about 24 cm². The dispensing plate includes a circular (11.35 mm diameter) orifice, which provides an inscribed circle diameter of 11.35 mm.

Container C is a dispensing container substantially similar to that of Container B. The dispensing plate of Container C includes an oval-shaped orifice with a major axis of 10 mm and a minor axis of 2 mm, which provides an inscribed circle diameter of 2 mm. The orifice of Container C lies within a finger divot.

Container D is a dispensing container substantially similar to that of Container B. The dispensing plate of Container D includes an oval-shaped orifice with a major axis of 2 mm and a minor axis of 1 mm, which provides an inscribed circle diameter of 1 mm. The orifice of Container D lies within a finger divot.

Container E is a conventional pump-type dispenser such as the 30 mL "Mezzo Top Fill" pump with actuator code A30-15 available from Megapumps L.P., Eatontown, N.J. Container E falls outside of the present invention because it destroys most the solid character of Example 1. The valve mechanism of Container E yields an orifice having an inscribed circle diameter of 0.5 mm.

Test Method and Results

This method provides a G' value for a given skin care composition (Examples 1-3) in a given container (Container A-E). For a dispensing container, dispense approximately 3 grams of the skin care composition onto a plastic weigh boat positioned on a top loading balance. If the dispense rate is controlled by the user, dispense the skin care composition at a constant rate of approximately 0.1 to 0.3 g/second. For a non-dispensing container (e.g., a jar), approximately 3 grams of skin care composition is carefully removed from the container using a using a suitable spatula and place onto a plastic weigh boat positioned on a top loading balance. Next, the skin care composition is carefully transferred to the rheometer plate while avoiding applying vigorous shear to the skin care composition.

Figure 6:
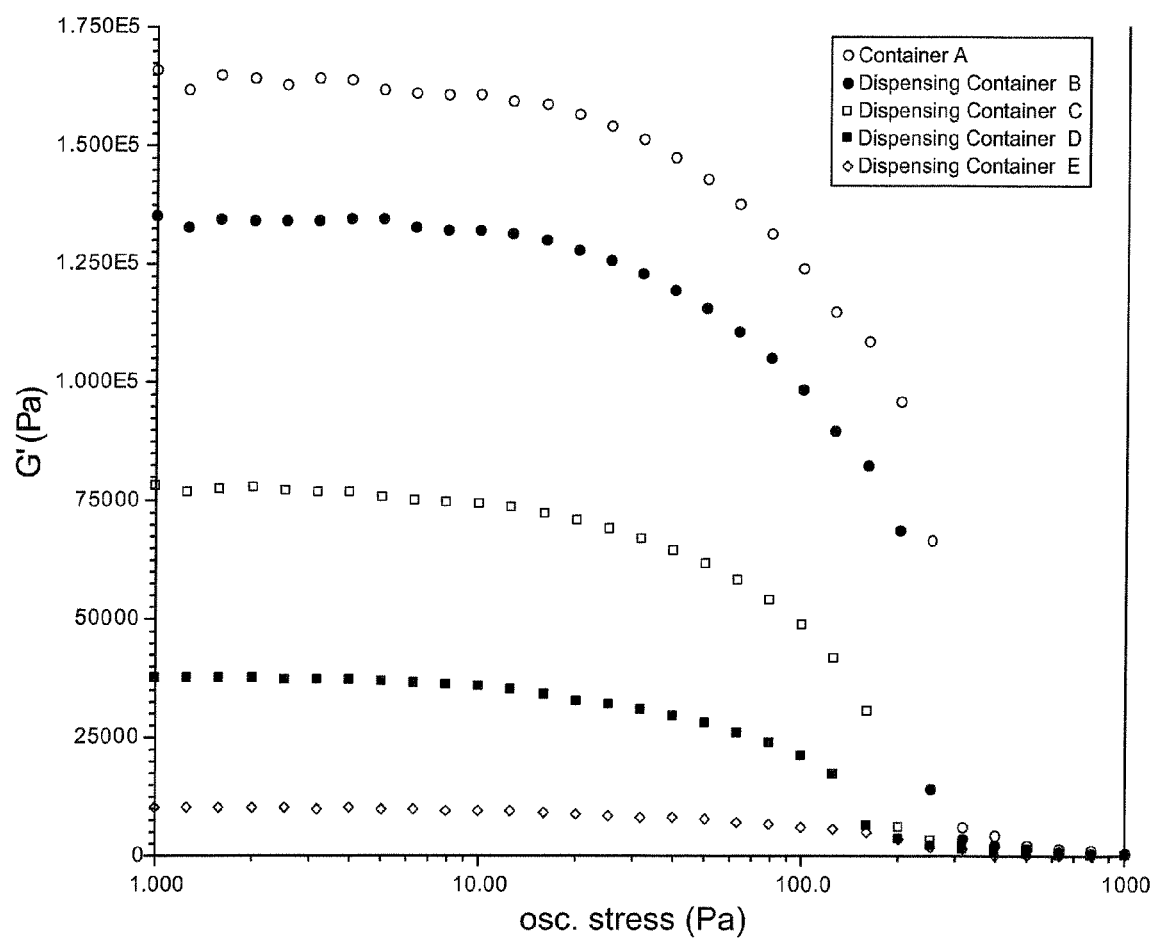
FIG. 6 is a graph showing G' values as a factor of oscillating stress for embodiments of the present invention and comparative examples.

A suitable rheometer for use in the present method is the AR 2000 Rheometer (available from TA Instruments, New Castle, Del.) interfaced with a computer having suitable software that provides data recordation and analysis. The test is performed at temperature of 25° C. and the equilibration time is 1 minute. The rheometer is configured with 4 cm diameter flat steel parallel plates at a gap setting of 1000 μm, an angular frequency of 50 rad/second, an oscillation stress sweep of 1-1000 Pa, log mode, and a sample rate of 10 points per decade. For each data sampling point, the conditioning and sampling times are 3 seconds, respectively. The interfaced computer and software provide the G' value as a factor of the stress; however, the G" values may also be collected. The G' values as recorded in the present invention (e.g., pre-dispense G' and post-dispense G') are an average of the initial seven readings of G' from the oscillation stress sweep as reported by the interfaced computer and software. FIG. 6 depicts a plot of the G' value as a factor of the stress for Example 1 within Containers A-E. The plots show how the G' of Example 1 is altered based on the particular container used. The G' with Container A is taken as the pre-dispense G' of Example 1. The other containers yield a post-dispense G' that preserves a percentage of the initial pre-dispense G'.

Table 1 provides G' values for Examples 1-3 in Containers A-E. The G' values associated with Container A are taken as the pre-dispense G' since container A is a non-dispensing container (i.e., jar). Containers B-E are dispensing container and, therefore, the G' values associated with these containers are taken as post-dispense G' values. Example 3 (i.e., the conventional skin care lotion) has little solid character as evidenced by G' value from Container A. The G' value for Example 3 is over two orders of magnitude less than the G' value of Examples 1 and 2 from Container A. Example 3 is outside the scope of the present invention given the low pre-dispense G'.

Containers B-D differ in the orifice size through which the skin care composition is dispensed. Examples 1 and 2 show a decreasing post-dispense G' as the inscribed circle diameter ("ICD") of the orifice decreases. For Example 1, Containers B, C, and D show a percent preservation of the initial pre-dispense G' of 81.7%, 47.1%, and 22.8%, respectively. For Example 2, Containers B, C, and D show a percent preservation of the initial pre-dispense G' of 86.7%, 35.7%, and 28.3%, respectively. It is believed that the orifice size as measured by the inscribed circle diameter may, in part, control the post-dispense G'.

Container E is a conventional pump having valve mechanism with an inscribed circle diameter of 0.5 mm. Container E shows an unacceptable percent preservation of the initial pre-dispense G' of 6.2%.

TABLE 1

|  | Example 1 | | Example 2 | | Example 3 |
| --- | --- | --- | --- | --- | --- |
|  | G' (Pa) | % Preservation | G' (Pa) | % Preservation | G' (Pa) |
| Container A | 164,000 | — | 95,300 | — | 962 |
| Dispensing Container B (ICD of 11.35 mm) | 134,000 | 81.7% | 82,600 | 86.7% | 803 |
| Dispensing Container C (ICD of 2 mm) | 77,200 | 47.1% | 34,000 | 35.7% | 798 |
| Dispensing Container D (ICD of 1 mm) | 37,400 | 22.8% | 27,000 | 28.3% | 927 |
| Dispensing Container E (ICD of 0.5 mm) | 10,200 | 6.2% | — |  | 897 |

* The G' values of each Example taken from Container A are taken as the pre-dispense G'.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care product comprising:
 a) a personal care composition having a pre-dispense G' of at least about 5,000 Pa, and
 b) a dispensing container having the personal care composition disposed therein, wherein said dispensing container comprises:
  i) a container body having a storage void, wherein the storage void contains the personal care composition;
  ii) a movable partition at least partially disposed within the storage void;
  iii) a drive mechanism connected to the movable partition, said drive mechanism advances the movable partition in contact with the personal care composition;
  iv) a dispensing plate joined to the container body; wherein the dispensing plate has an orifice through which the personal care composition is dispensed, wherein the orifice has an inscribed circle diameter of at least 1 mm;
 wherein the personal care product provides a G' preservation percentage of no less than 10%.

2. The personal care product of claim 1 wherein the personal care composition is in the form of a water-in-oil emulsion.

3. The personal care product of claim 1 wherein the personal care composition comprises from about 1% to about 75% of an aqueous phase.

4. The personal care product of claim 1 wherein the personal care composition comprises from about 0.1 to about 15% of a silicone elastomer.

5. The personal care product of claim 4 wherein the silicone elastomer is an emulsifying elastomer.

6. The personal care product of claim 1 wherein the personal care composition comprises from about 0.1 to about 40% of at least one solidifying agent.

7. The personal care product of claim 6 wherein the solidifying agent is a wax.

8. The personal care product of claim 7 wherein the wax is selected from a group consisting of silicone wax, polyethylene wax, and mixtures thereof.

9. The personal care product of claim 1 wherein the personal care composition comprises at least one skin care active selected from the group consisting of vitamin B compounds, vitamin C compounds, vitamin E compounds, peptides, sugar amines, oil control agents, skin lightening agents, hexamidine, and combinations thereof.

10. The personal care product of claim 1 wherein the personal care composition is substantially free of an antiperspirant actives and deodorant actives.

11. The personal care product of claim 1 wherein the drive mechanism advances the movable partition in a linear path.

12. The personal care product of claim 1 wherein the drive mechanism advances the movable partition in a rotational path.

13. The personal care product of claim 1 wherein the drive mechanism is screw lift mechanism comprising a feed screw operably connected to a hand wheel.

14. The personal care product of claim 1 wherein the drive mechanism is a hand wheel.

15. The personal care product of claim 14 wherein the dispensing plate is movably connected to the hand wheel.

16. The personal care product of claim 1 wherein the dispensing plate is non-convex.

17. The personal care product of claim 1 wherein the dispensing plate further comprises a finger divot proximate to the orifice.

* * * * *